United States Patent
Lee et al.

(10) Patent No.: US 9,546,221 B2
(45) Date of Patent: Jan. 17, 2017

(54) FUSION PROTEIN HAVING TRANSCRIPTION FACTOR TRANSACTIVATION-REGULATING DOMAIN AND PROTEIN TRANSDUCTION DOMAIN, AND TRANSCRIPTION FACTOR FUNCTION INHIBITOR COMPRISING THE SAME

(75) Inventors: San-Kyou Lee, Seoul (KR); Tae Yoon Park, Seoul (KR); Ye Kyung Seong, Seoul (KR); Jen Young Cho, Gyeonggi-do (KR); Jong Hyun Park, Seoul (KR); Sang Hwa Yang, Seoul (KR)

(73) Assignee: Sang-Kyou Lee, Seoul (KR)

( * ) Notice: Subject to any disclaimer, the term of this patent is extended or adjusted under 35 U.S.C. 154(b) by 149 days.

(21) Appl. No.: 13/818,062

(22) PCT Filed: Aug. 19, 2011

(86) PCT No.: PCT/KR2011/006158
§ 371 (c)(1),
(2), (4) Date: Apr. 4, 2013

(87) PCT Pub. No.: WO2012/023838
PCT Pub. Date: Feb. 23, 2012

(65) Prior Publication Data
US 2013/0231274 A1 Sep. 5, 2013

(30) Foreign Application Priority Data

Aug. 20, 2010 (KR) .................. 10-2010-0080864
Dec. 10, 2010 (KR) .................. 10-2010-0126455

(51) Int. Cl.
C07K 19/00 (2006.01)
C07K 14/47 (2006.01)
C12N 15/62 (2006.01)

(52) U.S. Cl.
CPC ........... *C07K 19/00* (2013.01); *C07K 14/4703* (2013.01); *C12N 15/62* (2013.01); *C07K 2319/10* (2013.01); *C07K 2319/70* (2013.01); *C07K 2319/73* (2013.01); *C07K 2319/80* (2013.01); *C07K 2319/81* (2013.01)

(58) Field of Classification Search
None
See application file for complete search history.

(56) References Cited

U.S. PATENT DOCUMENTS

2007/0178113 A1* 8/2007 Backstrom et al. ........ 424/185.1
2010/0323383 A1* 12/2010 Manel et al. .............. 435/29

OTHER PUBLICATIONS

Lim, Se Jin et al., "Protein transduction domain (PTD) and its application", BioWave, 2006, vol. 8, No. 14, pp. 1-17.*
Bruno, L. et al., "Runx proteins regulate Foxp3 expression", Jottr. Exp. Med., Epub Oct. 19, 2009 vol. 206, No. 11, pp. 2329-2337.*
Youn, J.-L et al., "Enhanced delivery efficiency of recombinant adenovirus into tumor and mesenchymal stem cells by a novel PTD", Cancer Gene Ther., Nov. 2008, vol. 15, No. 11, pp. 703-712.*
Villard, J., "Transcription regulation and human diseases", Swiss Med. Wkly, 2004, vol. 134, pp. 571-579.*
Bruno, L. et al., "Runx proteins regulate Foxp3 expression", M. Exp. Med., Epub Oct. 19, 2009 vol. 206, No. 11, pp. 2329-2337.
Youn, J. et al., "Enhanced delivery efficiency of recombinant adenovirus into tumor and mesenchymal stem cells by a novel PTD", Cancer Gene Ther., Nov. 2008, vol. 15, No. 11, pp. 703-712.
Park et al., "RORγt-specific transcriptional interactomic inhibition suppresses autoimmunity associated with $T_H17$ cells." PNAS (2014) vol. 111, No. 52: 18673-18678.

* cited by examiner

Primary Examiner — Maury Audet
(74) Attorney, Agent, or Firm — Mintz Levin Cohn Ferris Glovsky and Popeo, P.C.; Kongsik Kim; Richard B. Emmons

(57) ABSTRACT

This invention relates to a fusion protein comprising the TMD of the transcription factor and PTD, an inhibitor for transcription factor function comprising the same, and a method for producing the same. Various diseases associated with malfunctions or defects of the transcription factor are effectively treated using the fusion protein according to the present invention.

9 Claims, 17 Drawing Sheets

1. PBS
2. OVA
3. OVA+Hph-1-GT3-DBD
4. OVA+Hph-1-EGFP

SEQUENCE LISTING

<160> NUMBER OF SEQ ID NOS: 11

<210> SEQ ID NO 1
<211> LENGTH: 11
<212> TYPE: PRT
<213> ORGANISM: Artificial Sequence
<220> FEATURE:
<223> OTHER INFORMATION: Hph-1

<400> SEQUENCE: 1

Tyr Ala Arg Val Arg Arg Arg Gly Pro Arg Arg
1               5                   10

<210> SEQ ID NO 2
<211> LENGTH: 99
<212> TYPE: PRT
<213> ORGANISM: Artificial Sequence
<220> FEATURE:
<223> OTHER INFORMATION: RORgammat DNA binding domain

<400> SEQUENCE: 2

Met Arg Thr Gln Ile Glu Val Ile Pro Cys Lys Ile Cys Gly Asp Lys
1               5                   10                  15

Ser Ser Gly Ile His Tyr Gly Val Ile Thr Cys Glu Gly Cys Lys Gly
            20                  25                  30

Phe Phe Arg Arg Ser Gln Gln Cys Asn Val Ala Tyr Ser Cys Thr Arg
        35                  40                  45

Gln Gln Asn Cys Pro Ile Asp Arg Thr Ser Arg Asn Arg Cys Gln His
    50                  55                  60

Cys Arg Leu Gln Lys Cys Leu Ala Leu Gly Met Ser Arg Asp Ala Val
65                  70                  75                  80

Lys Phe Gly Arg Met Ser Lys Lys Gln Arg Asp Ser Leu His Ala Glu
                85                  90                  95

Val Gln Lys

<210> SEQ ID NO 3
<211> LENGTH: 108
<212> TYPE: PRT
<213> ORGANISM: Artificial Sequence
<220> FEATURE:
<223> OTHER INFORMATION: Gata3 DNA binding domain

<400> SEQUENCE: 3

Cys Val Asn Cys Gly Ala Thr Ser Thr Pro Leu Trp Arg Arg Asp Gly
1               5                   10                  15

Thr Gly His Tyr Leu Cys Asn Ala Cys Gly Leu Tyr His Lys Met Asn
            20                  25                  30

Gly Gln Asn Arg Pro Leu Ile Lys Pro Lys Arg Arg Leu Ser Ala Ala
        35                  40                  45

Arg Arg Ala Gly Thr Ser Cys Ala Asn Cys Gln Thr Thr Thr Thr Thr
    50                  55                  60

Leu Trp Arg Arg Asn Ala Asn Gly Asp Pro Val Cys Asn Ala Cys Gly
65                  70                  75                  80

Leu Tyr Tyr Lys Leu His Asn Ile Asn Arg Pro Leu Thr Met Lys Lys
                85                  90                  95

Glu Gly Ile Gln Thr Arg Asn Arg Lys Met Ser Ser
            100                 105

<210> SEQ ID NO 4
<211> LENGTH: 201

```
<212> TYPE: PRT
<213> ORGANISM: Artificial Sequence
<220> FEATURE:
<223> OTHER INFORMATION: Tbet DNA binding domain

<400> SEQUENCE: 4

Tyr Ala Leu Pro Ala Gly Leu Glu Val Ser Gly Lys Leu Arg Val Ala
1               5                   10                  15

Leu Ser Asn His Leu Leu Trp Ser Lys Phe Asn Gln His Gln Thr Glu
            20                  25                  30

Met Ile Ile Thr Lys Gln Gly Arg Arg Met Phe Pro Phe Leu Ser Phe
        35                  40                  45

Thr Val Ala Gly Leu Glu Pro Thr Ser His Tyr Arg Met Phe Val Asp
    50                  55                  60

Val Val Leu Val Asp Gln His His Trp Arg Tyr Gln Ser Gly Lys Trp
65                  70                  75                  80

Val Gln Cys Gly Lys Ala Glu Gly Ser Met Pro Gly Asn Arg Leu Tyr
                85                  90                  95

Val His Pro Asp Ser Pro Asn Thr Gly Ala His Trp Met Arg Gln Glu
            100                 105                 110

Val Ser Phe Gly Lys Leu Lys Leu Thr Asn Asn Lys Gly Ala Ser Asn
        115                 120                 125

Asn Val Thr Gln Met Ile Val Leu Gln Ser Leu His Lys Tyr Gln Pro
    130                 135                 140

Arg Leu His Ile Val Glu Val Asn Asp Gly Glu Pro Glu Ala Ala Cys
145                 150                 155                 160

Ser Ala Ser Asn Thr His Val Phe Thr Phe Gln Glu Thr Gln Phe Ile
                165                 170                 175

Ala Val Thr Ala Tyr Gln Asn Ala Glu Ile Thr Gln Leu Lys Ile Asp
            180                 185                 190

Asn Asn Pro Phe Ala Lys Gly Phe Arg
        195                 200

<210> SEQ ID NO 5
<211> LENGTH: 94
<212> TYPE: PRT
<213> ORGANISM: Artificial Sequence
<220> FEATURE:
<223> OTHER INFORMATION: Foxp3 DNA binding domain(F)

<400> SEQUENCE: 5

Leu Arg Pro Pro Phe Thr Tyr Ala Thr Leu Ile Arg Trp Ala Ile Leu
1               5                   10                  15

Glu Ala Pro Glu Arg Gln Arg Thr Leu Asn Glu Ile Tyr His Trp Phe
            20                  25                  30

Thr Arg Met Phe Ala Tyr Phe Arg Asn His Pro Ala Thr Trp Lys Asn
        35                  40                  45

Ala Ile Arg His Asn Leu Ser Leu His Lys Cys Phe Val Arg Val Glu
    50                  55                  60

Ser Glu Lys Gly Ala Val Trp Thr Val Asp Glu Phe Glu Phe Arg Lys
65                  70                  75                  80

Lys Arg Ser Gln Arg Pro Asn Lys Cys Ser Asn Pro Cys Pro
                85                  90

<210> SEQ ID NO 6
<211> LENGTH: 197
<212> TYPE: PRT
<213> ORGANISM: Artificial Sequence
```

<220> FEATURE:
<223> OTHER INFORMATION: Foxp3 repressor domain(R)

<400> SEQUENCE: 6

Met Pro Asn Pro Arg Pro Ala Lys Pro Met Ala Pro Ser Leu Ala Leu
1               5                   10                  15

Gly Pro Ser Pro Gly Val Leu Pro Ser Trp Lys Thr Ala Pro Lys Gly
            20                  25                  30

Ser Glu Leu Leu Gly Thr Arg Gly Ser Gly Pro Phe Gln Gly Arg
        35                  40                  45

Asp Leu Arg Ser Gly Ala His Thr Ser Ser Leu Asn Pro Leu Pro
    50                  55                  60

Pro Ser Gln Leu Gln Leu Pro Thr Val Pro Leu Val Met Val Ala Pro
65                  70                  75                  80

Ser Gly Ala Arg Leu Gly Pro Ser Pro His Leu Gln Ala Leu Leu Gln
                85                  90                  95

Asp Arg Pro His Phe Met His Gln Leu Ser Thr Val Asp Ala His Ala
            100                 105                 110

Gln Thr Pro Val Leu Gln Val Arg Pro Leu Asp Asn Pro Ala Met Ile
        115                 120                 125

Ser Leu Pro Pro Pro Ser Ala Ala Thr Gly Val Phe Ser Leu Lys Ala
    130                 135                 140

Arg Pro Gly Leu Pro Pro Gly Ile Asn Val Ala Ser Leu Glu Trp Val
145                 150                 155                 160

Ser Arg Glu Pro Ala Leu Leu Cys Thr Phe Pro Arg Ser Gly Thr Pro
                165                 170                 175

Arg Lys Asp Ser Asn Leu Leu Ala Ala Pro Gln Gly Ser Tyr Pro Leu
            180                 185                 190

Leu Ala Asn Gly Val
        195

<210> SEQ ID NO 7
<211> LENGTH: 141
<212> TYPE: PRT
<213> ORGANISM: Artificial Sequence
<220> FEATURE:
<223> OTHER INFORMATION: tRORgammat-TMD

<400> SEQUENCE: 7

His His His His His Ala Ser Tyr Ala Arg Val Arg Arg Arg Gly
1               5                   10                  15

Pro Arg Arg Gly Ser Tyr Ala Val Arg Arg Gly Pro Arg Arg
            20                  25                  30

Glu Leu Met Arg Thr Gln Ile Glu Val Ile Pro Cys Lys Ile Cys Gly
        35                  40                  45

Asp Lys Ser Ser Gly Ile His Tyr Gly Val Ile Thr Cys Glu Gly Cys
    50                  55                  60

Lys Gly Phe Phe Arg Arg Ser Gln Cys Asn Val Ala Tyr Ser Cys
65                  70                  75                  80

Thr Arg Gln Gln Asn Cys Pro Ile Asp Arg Thr Ser Arg Asn Arg Cys
                85                  90                  95

Gln His Cys Arg Leu Gln Lys Cys Leu Ala Leu Gly Met Ser Arg Asp
            100                 105                 110

Ala Val Lys Phe Gly Arg Met Ser Lys Lys Gln Arg Asp Ser Leu His
        115                 120                 125

Ala Glu Val Gln Lys Ala Tyr Lys Asp Asp Asp Asp Lys

<210> SEQ ID NO 8
<211> LENGTH: 160
<212> TYPE: PRT
<213> ORGANISM: Artificial Sequence
<220> FEATURE:
<223> OTHER INFORMATION: tGata3-TMD

<400> SEQUENCE: 8

```
Met Arg Gly Ser His His His His His His Gly Met Ala Ser Gly Tyr
 1               5                  10                  15

Ala Arg Val Arg Arg Gly Pro Arg Gly Gly Ser Tyr Ala Arg
             20                  25                  30

Val Arg Arg Gly Pro Arg Arg Glu Phe Cys Val Asn Cys Gly Ala
             35                  40                  45

Thr Ser Thr Pro Leu Trp Arg Arg Asp Gly Thr Gly His Tyr Leu Cys
         50                  55                  60

Asn Ala Cys Gly Leu Tyr His Lys Met Asn Gly Gln Asn Arg Pro Leu
 65                  70                  75                  80

Ile Lys Pro Lys Arg Arg Leu Ser Ala Ala Arg Arg Ala Gly Thr Ser
                 85                  90                  95

Cys Ala Asn Cys Gln Thr Thr Thr Thr Thr Leu Trp Arg Arg Asn Ala
            100                 105                 110

Asn Gly Asp Pro Val Cys Asn Ala Cys Gly Leu Tyr Tyr Lys Leu His
            115                 120                 125

Asn Ile Asn Arg Pro Leu Thr Met Lys Lys Glu Gly Ile Gln Thr Arg
        130                 135                 140

Asn Arg Lys Met Ser Ser Leu Glu Asp Tyr Lys Asp Asp Asp Asp Lys
145                 150                 155                 160
```

<210> SEQ ID NO 9
<211> LENGTH: 261
<212> TYPE: PRT
<213> ORGANISM: Artificial Sequence
<220> FEATURE:
<223> OTHER INFORMATION: tTbet-TMD

<400> SEQUENCE: 9

```
Met Arg Gly Ser His His His His His His Gly Met Ala Ser Met Thr
 1               5                  10                  15

Gly Gly Gln Gln Met Gly Arg Asp Leu Tyr Asp Asp Asp Lys Asp
             20                  25                  30

Pro Ser Ser Arg Ser Gly Tyr Ala Arg Val Arg Arg Gly Pro Arg
         35                  40                  45

Arg Gly Ser Arg Tyr Ala Leu Pro Ala Gly Leu Glu Val Ser Gly Lys
     50                  55                  60

Leu Arg Val Ala Leu Ser Asn His Leu Leu Trp Ser Lys Phe Asn Gln
 65                  70                  75                  80

His Gln Thr Glu Met Ile Ile Thr Lys Gln Gly Arg Arg Met Phe Pro
                 85                  90                  95

Phe Leu Ser Phe Thr Val Ala Gly Leu Glu Pro Thr Ser His Tyr Arg
            100                 105                 110

Met Phe Val Asp Val Val Leu Val Asp Gln His His Trp Arg Tyr Gln
            115                 120                 125

Ser Gly Lys Trp Val Gln Cys Gly Lys Ala Glu Gly Ser Met Pro Gly
        130                 135                 140
```

Asn Arg Leu Tyr Val His Pro Asp Ser Pro Asn Thr Gly Ala His Trp
145                 150                 155                 160

Met Arg Gln Glu Val Ser Phe Gly Lys Leu Lys Leu Thr Asn Asn Lys
                165                 170                 175

Gly Ala Ser Asn Asn Val Thr Gln Met Ile Val Leu Gln Ser Leu His
                180                 185                 190

Lys Tyr Gln Pro Arg Leu His Ile Val Glu Val Asn Asp Gly Glu Pro
            195                 200                 205

Glu Ala Ala Cys Ser Ala Ser Asn Thr His Val Phe Thr Phe Gln Glu
            210                 215                 220

Thr Gln Phe Ile Ala Val Thr Ala Tyr Gln Asn Ala Glu Ile Thr Gln
225                 230                 235                 240

Leu Lys Ile Asp Asn Asn Pro Phe Ala Lys Gly Phe Arg Asp Tyr Lys
                245                 250                 255

Asp Asp Asp Lys
            260

<210> SEQ ID NO 10
<211> LENGTH: 154
<212> TYPE: PRT
<213> ORGANISM: Artificial Sequence
<220> FEATURE:
<223> OTHER INFORMATION: tFoxp3-F-TMD

<400> SEQUENCE: 10

Met Gly Ser Ser His His His His His His Ser Ser Gly Leu Val Pro
1               5                   10                  15

Arg Gly Ser His Met Ala Ser Gly Tyr Ala Arg Val Arg Arg Arg Gly
                20                  25                  30

Pro Arg Arg Gly Gly Ser Tyr Ala Arg Val Arg Arg Gly Pro Arg
            35                  40                  45

Arg Gly Tyr Pro Tyr Asp Val Pro Asp Tyr Ala Lys Leu Arg Pro Pro
        50                  55                  60

Phe Thr Tyr Ala Thr Leu Ile Arg Trp Ala Ile Leu Glu Ala Pro Glu
65              70                  75                  80

Arg Gln Arg Thr Leu Asn Glu Ile Tyr His Trp Phe Thr Arg Met Phe
                85                  90                  95

Ala Tyr Phe Arg Asn His Pro Ala Thr Trp Lys Asn Ala Ile Arg His
            100                 105                 110

Asn Leu Ser Leu His Lys Cys Phe Val Arg Val Glu Ser Glu Lys Gly
        115                 120                 125

Ala Val Trp Thr Val Asp Glu Phe Glu Phe Arg Lys Lys Arg Ser Gln
    130                 135                 140

Arg Pro Asn Lys Cys Ser Asn Pro Cys Pro
145                 150

<210> SEQ ID NO 11
<211> LENGTH: 258
<212> TYPE: PRT
<213> ORGANISM: Artificial Sequence
<220> FEATURE:
<223> OTHER INFORMATION: tFoxp3-R-TMD

<400> SEQUENCE: 11

Met Gly Ser Ser His His His His His His Ser Ser Gly Leu Val Pro
1               5                   10                  15

Arg Gly Ser His Met Ala Ser Gly Tyr Ala Arg Val Arg Arg Arg Gly
                20                  25                  30

-continued

```
Pro Arg Arg Gly Gly Ser Tyr Ala Arg Val Arg Arg Arg Gly Pro Arg
        35                  40                  45
Arg Gly Tyr Pro Tyr Asp Val Pro Asp Tyr Ala Lys Leu Met Pro Asn
        50                  55                  60
Pro Arg Pro Ala Lys Pro Met Ala Pro Ser Leu Ala Leu Gly Pro Ser
65              70                  75                  80
Pro Gly Val Leu Pro Ser Trp Lys Thr Ala Pro Lys Gly Ser Glu Leu
            85                  90                  95
Leu Gly Thr Arg Gly Ser Gly Gly Pro Phe Gln Gly Arg Asp Leu Arg
            100             105             110
Ser Gly Ala His Thr Ser Ser Ser Leu Asn Pro Leu Pro Pro Ser Gln
            115             120             125
Leu Gln Leu Pro Thr Val Pro Leu Val Met Val Ala Pro Ser Gly Ala
        130             135             140
Arg Leu Gly Pro Ser Pro His Leu Gln Ala Leu Leu Gln Asp Arg Pro
145             150             155             160
His Phe Met His Gln Leu Ser Thr Val Asp Ala His Ala Gln Thr Pro
                165             170             175
Val Leu Gln Val Arg Pro Leu Asp Asn Pro Ala Met Ile Ser Leu Pro
            180             185             190
Pro Pro Ser Ala Ala Thr Gly Val Phe Ser Leu Lys Ala Arg Pro Gly
        195             200             205
Leu Pro Pro Gly Ile Asn Val Ala Ser Leu Glu Trp Val Ser Arg Glu
    210             215             220
Pro Ala Leu Leu Cys Thr Phe Pro Arg Ser Gly Thr Pro Arg Lys Asp
225             230             235             240
Ser Asn Leu Leu Ala Ala Pro Gln Gly Ser Tyr Pro Leu Leu Ala Asn
            245             250             255
Gly Val
```

FUSION PROTEIN HAVING TRANSCRIPTION FACTOR TRANSACTIVATION-REGULATING DOMAIN AND PROTEIN TRANSDUCTION DOMAIN, AND TRANSCRIPTION FACTOR FUNCTION INHIBITOR COMPRISING THE SAME

CROSS-REFERENCES TO RELATED APPLICATIONS

This application is a U.S. national phase application, pursuant to 35 U.S.C. §371, of PCT/KR2011/006158, filed Aug. 19, 2011, designating the United States, which claims priority to Korean Application No. 10-2010-0080864, filed Aug. 20, 2010, and Korean Application No. 10-2010-0126455, filed Dec. 10, 2010. The entire contents of the aforementioned patent applications are incorporated herein by this reference.

SEQUENCE LISTING

The instant application contains a Sequence Listing which has been submitted in ASCII format via EFS-Web and is hereby incorporated by reference in its entirety. Said ASCII copy, created on May 8, 2013, is named 92438-301264-Sequence_Listing_ST25.txt and is 16,264 bytes in size.

TECHNICAL FIELD

The present invention relates to a fusion protein having protein transcription factor transactivation-regulating domain and protein transduction domain, and an inhibitor for a transcription factor function comprising the same.

BACKGROUND ART

Transcription factor is an element to control the transcription of a gene which can modulate the transcriptional activity through binding to specific sequences in DNA or binding to other factor(s). If this binding or interaction does not function correctly, various diseases associated with the malfunctions or defects of the transcription factor could be induced.

In 1998, the identity of Protein Transduction Domain (PTD) was originally reported in that a part of HIV-TAT protein can facilitate the delivery of BRM (Biological Response Modifier) into the cells. About 50 different PTDs have been discovered so far, and Tat, VP22, Antp HP4 and Hph-1 have been used frequently for basic and therapeutic research. It has been demonstrated that these PTDs effectively deliver a protein bigger than 120 kDa into the cells within a short period of time, and DNA/RNA or the undeliverable chemical compound can be transduced into the cells by PTD. PTD is a novel drug delivery system to facilitate intracellular delivery of the BRM into the brain across BBB (Blood Brain Barrier) or into the body through a local administration route such as skin, intranasal or ocular pathway.

Therefore, this inventor completes the generation of the fusion protein comprising the part of a transcription factor and PTD on the basis of the fact that the transcription factor exerts the function(s) through its interaction with DNA or other proteins.

DETAILED DESCRIPTION

Technical Purpose

The present invention is intended to provide an inhibitor for transcription factor function comprising TMD of transcription factor and PTD, and to provide a pharmaceutical composition for treating diseases associated with malfunctions or defects of the transcription factor comprising said fusion protein and pharmaceutically acceptable excipients.

In addition, the present invention is intended to provide a method for treating the diseases associated with malfunctions or defects of the transcription factor in a human, comprising administering to said human an effective amount of the fusion protein comprising the TMD of the transcription factor and PTD.

In addition, the present invention is intended to provide a fusion protein comprising the TMD of the transcription factor and PTD, nucleic acids encoding said fusion protein, vectors comprising said nucleic acids, and host cells comprising said vectors.

In addition, the present invention is intended to provide a method for producing a fusion protein, comprising a step of expressing the vector comprising the gene encoding TMD of the transcription factor and the gene encoding PTD in the host cells.

Technical Solution

In one embodiment of the present invention, TMD (Transcription Modulation Domain) refers to a part of a transcription factor which is involved in functional interaction with molecules or factors important during transcription such as, but not limited to, DNA, RNA, transcriptional co-activator, transcriptional repressor, enhancer-binding factor or ligand, or in dimerization/multimerization or nuclear localization.

In one embodiment, the present invention provides an inhibitor for transcription factor function comprising the fusion protein comprising TMD of transcription factor and PTD. In addition, the transcription factor in the embodiment is selected from the group consisting of RORγt (Retinoic acid-related orphan receptor gamma t), Tbet (T-box 21), GATA-3 (GATA binding protein 3), FOXP3 (Forkhead box P3), RORα4 (Retinoic acid-related orphan receptor alpha 4), HIF-1/2α (Hypoxia inducible factor 1/2α), STAT (Signal transducers and activators of transcription), PPARγ (peroxisome proliferator-activated receptor gamma), p53, AP-1, NFκB (nuclear factor kappa-B), NKx2.5 (NK2 transcription factor related, locus 5), FOXO (Forkhead box O), RELA (v-rel reticuloendotheliosis viral oncogene homolog A) or Runx (runt-related transcription factor). In addition, the transcription factor in the embodiment is selected from the group consisting of RORγt (Retinoic acid-related orphan receptor gamma t), Tbet (T-box 21), GATA-3 (GATA binding protein 3) and FOXP3 (Forkhead box P3). In addition, PTD in the embodiment is selected from the group consisting of HP4, Hph-1, Mph-1, Sim-2, Tat, VP22, Antp (Antennapedia), Pep-1 (peptide), PTD-5, R9 (arginine), 7R and CTP (Cytoplasmic Transduction Peptide). PTD in the embodiment may have amino acid sequences of SEQ ID NO: 1. TMD of transcription factor in the embodiment may be DNA binding domain or protein interaction domain. TMD of the transcription factor comprises one or more selected from the group consisting of helix-turn-helix domain, zinc finger domain, leucine zipper domain, winged helix domain, winged helix turn helix domain, helix-loop-helix domain, HMG-box domain and forkhead domain.

TMD of the transcription factor comprises one or more selected from the group consisting of the domain interacting with DNA, RNA, transcriptional co-activator, transcriptional repressor, enhancer-binding factor and ligand, the domain involved in dimerization/multimerization and the domain involved in nuclear localization. TMD of the transcription factor may have the sequences of SEQ ID NOs: 2 to 6. TMD of the transcription factor may have the sequences of SEQ ID NOs: 7 to 11.

In one embodiment, the present invention provides a fusion protein comprising TMD of transcription factor and PTD. In addition, the transcription factor in the embodiment is selected from the group consisting of RORγt (Retinoic acid-related orphan receptor gamma t), Tbet (T-box 21), GATA-3 (GATA binding protein 3), FOXP3 (Forkhead box P3), RORα4 (Retinoic acid-related orphan receptor alpha 4), HIF-1/2α (Hypoxia inducible factor 1/2α), STAT (Signal transducers and activators of transcription), PPARγ (peroxisome proliferator-activated receptor gamma), p53, AP-1, NFκB (nuclear factor kappa-B), NK×2.5 (NK2 transcription factor related, locus 5), FOXO (Forkhead box O), RELA (v-rel reticuloendotheliosis viral oncogene homolog A) and Runx (runt-related transcription factor). In addition, the transcription factor in the embodiment is selected from the group consisting of RORγt (Retinoic acid-related orphan receptor gamma t), Tbet (T-box 21), GATA-3 (GATA binding protein 3) and FOXP3 (Forkhead box P3). In addition, PTD in the embodiment is selected from the group consisting of HP4, Hph-1, Mph-1, Sim-2, Tat, VP22, Antp (Antennapedia), Pep-1 (peptide), PTD-5, R9 (arginine), 7R and CTP (Cytoplasmic Transduction Peptide). PTD in the embodiment may have the amino acid sequences of SEQ ID NO: 1. TMD of transcription factor in the embodiment may be DNA binding domain or protein interaction domain. TMD of the transcription factor comprises one or more selected from the group consisting of helix-turn-helix domain, zinc finger domain, leucine zipper domain, winged helix domain, winged helix turn helix domain, helix-loop-helix domain, HMG-box domain and forkhead domain. TMD of the transcription factor comprises one or more selected from the group consisting of the domain interacting with DNA, RNA, transcriptional co-activator, transcriptional repressor, enhancer-binding factor and ligand, the domain involved in dimerization/multimerization and the domain involved in nuclear localization. TMD of the transcription factor may have the sequences of SEQ ID NOs: 2 to 6. TMD of the transcription factor may have the sequences of SEQ ID NOs: 7 to 11. In addition, the present invention provides a nucleic acid encoding said fusion protein, a vector comprising said nucleic acid and a host cell comprising said vector. PTD in the embodiment may have the sequence of SEQ ID NO: 1. TMD of the transcription factor may have the sequences of SEQ ID NOs: 2 to 6. The fusion protein in the host cell may have the sequences of SEQ ID NOs 7 to 11. The host cell may be BL21 star (DE3) pLys S.

In one embodiment, the present invention provides a method for producing the fusion protein by expressing the vector which combines the gene encoding TMD of the transcription factor and the gene encoding PTD in the host cells.

In one embodiment, the present invention provides a pharmaceutical composition for treating diseases associated with malfunctions or defects of the transcription factor, comprising the fusion protein comprising TMD of the transcription factor and PTD, and pharmaceutical acceptable excipients. When the transcription factor in the embodiment is NK×2.5 (NK2 transcription factor related, locus 5) or HIF-1α (Hypoxia inducible factor 1α), the disease associated with malfunctions or defects of the transcription factor may be a neurological disease. When the transcription factor in the embodiment is HIF-1α (Hypoxia inducible factor 1α), the disease associated with malfunctions or defects of the transcription factor may be a neurological disease. When the transcription factor in the embodiment is PPARγ (peroxisome proliferator-activated receptor gamma), the disease associated with malfunctions or defects of the transcription factor may be diabetes. When the transcription factor in the embodiment is RORγt (Retinoic acid-related orphan receptor gamma t), RORα4 (Retinoic acid-related orphan receptor alpha 4) or FOXO (Forkhead box O), the disease associated with malfunctions or defects of the transcription factor may be an autoimmune disease or inflammatory disease. When the transcription factor in the embodiment is HIF-2α (Hypoxia inducible factor 2α) or STAT (Signal transducers and activators of transcription), the disease associated with malfunctions or defects of transcription factor may be an autoimmune disease or inflammatory disease. When the transcription factor in the embodiment is AP-1 or NFκB (nuclear factor kappa-B), the disease associated with malfunctions or defects of the transcription factor may be a vascular disease or inflammatory disease. When the transcription factor is p53, SP1 or RELA (v-rel reticuloendotheliosis viral oncogene homolog A), the disease associated with malfunctions or defects of the transcription factor may be cancer. When the transcription factor in the embodiment is GATA-3 (GATA binding protein 3), the disease associated with malfunctions or defects of the transcription factor may be asthma or atopy. When the transcription factor in the embodiment is RORγt, the disease associated with malfunctions or defects of the transcription factor may be EAE (MS), RA or IBD (Crohn's disease). When the transcription factor in the embodiment is Foxp3, the disease associated with malfunctions or defects of the transcription factor may be cancer. When the transcription factor in the embodiment is Tbet, the disease associated with malfunctions or defects of the transcription factor may be RA, IBD (Crohn's disease) or EAE (MS).

Advantageous Effects

The fusion protein according to the present invention can be used to treat various diseases associated with malfunctions or defects of the transcription factor.

MODE FOR INVENTION

Example 1

Figure 1:
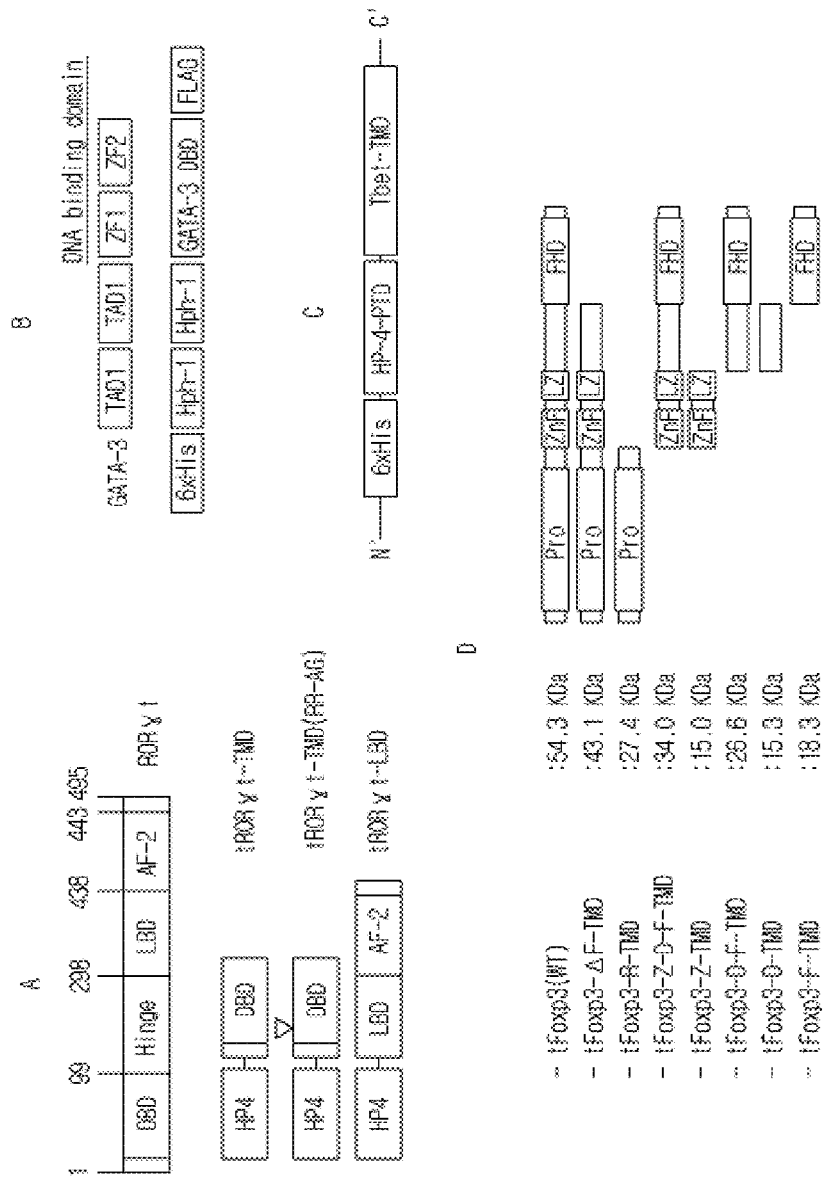
FIG. 1 shows the structure of the proteins used as one embodiment according to the present invention, the fusion protein between RORγt-TMD and Hph-1-PTD (hereafter, it will be referred to as tRORγt-TMD), RORγt-TMD itself without Hph-1-PTD that cannot be transduced into cells because Hph-1-PTD is not present, the fusion protein RORγt-TMD that has LBD (Ligand Binding Domain) instead of RORgt-TMD.
Figure 2:
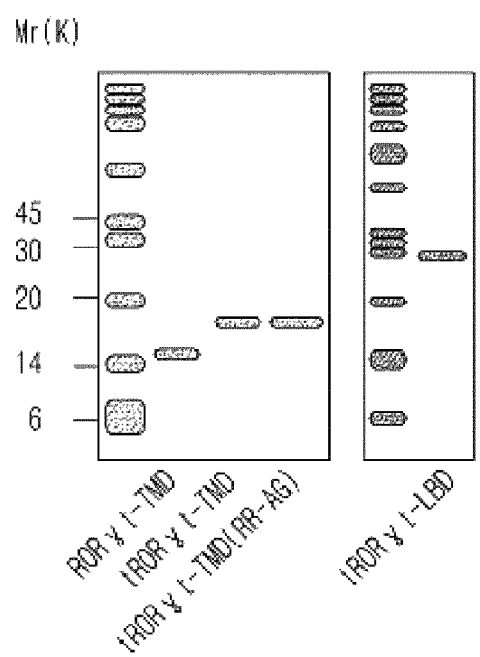
FIG. 2 shows the pictures of the coomassie blue staining for tRORγt-TMD, RORγt-TMD, and tRORγt-LBD used as one embodiment according to the present invention.

Generation, Separation and Purification of the Fusion Protein Comprising TMD of a Transcription Factor and PTD The DNA fragment encoding RORγt-TMD domain that controls transcriptional activity (SEQ ID NO: 2, the domain of controlling transcriptional activity in transcription factor RORγt) or that encoding RORγt-LBD was made by PCR, and the three recombinant DNA constructs such as tRORγt-TMD comprising Hph-1-PTD and RORγt-TMD, tRORγt-LBD comprising Hph-1-PTD and RORγt-LBD, and RORγt-TMD which does not have Hph-1-PTD are produced by recombinant DNA technology (FIG. 1). Three recombinant DNAs were cloned in pRSETb vector and were used to transform BL21 star (DE3) pLysS competent cell. We induced the expression of tRORγt-TMD, tRORγt-LBD and RORγt-TMD fusion protein by adding 1 mM IPTG (isopropyl-β-D-thiogalactopyranoside) after culture of the transformed competent cell. The cultured cells were then collected and sonicated by a sonicator after dissolving by lysis buffer (10 mM imidazole, 300 mM NaCl, 50 mM NaH2PO4, pH 8.0). The fusion proteins were combined with a Ni-NTA bead through 6× histidine in the forepart of tRORγt-TMD, tRORγt-LBD or RORγt-TMD fusion proteins. And then, we placed the fusion proteins into the column having Ni-NTA beads, washed the column with wash buffer (30 mM imidazole, 300 mM NaCl, 50 mM NaH2PO4, pH 8.0), and then isolated the fusion proteins with elution buffer (3M imidazole, 300 mM NaCl, 50 mM NaH2PO4, pH 8.0). We removed Nacl and imidazole through changing the buffer into 10% glycerol PBS by using PD-10. Then, we re-purified the fusion proteins through SP bead in order to remove endotoxins such as LPS in collected proteins. The proteins were bound to the beads in the binding buffer (300 mM NaCl, 50 mM NaH2PO4, pH 7.2), then put into the column, isolated by the elution buffer (2M NaCl, 50 mM NaH2PO4, pH 8.0). Finally, we removed NaCl in the fraction containing the fusion proteins and changed the buffer into PBS, then flash-froze at −80° C. We analyzed the size and purity of these fusion proteins by analyzing purified tRORγt-TMD, tRORγt-LBD or RORγt-TMD fusion protein in SDS-PAGE (FIG. 2).

tGT3-TMD comprising Hph-1-PTD and the transcription modulation domain (SEQ ID NO: 3) of GATA-3, tTbet-TMD comprising Hph-1-PTD and the transcription modulation domain (SEQ ID NO: 4) of Tbet, and tFoxp3-TMD comprising Hph-1-PTD and the transcription modulation domain (SEQ ID NOs: 5 and 6) of Foxp3 (refer to FIGS. 1b, 1c and 1d) were made in accordance with the above method.

Example 2

Confirmation of Intracellular Delivery of the Fusion Protein

<2-1. Confirmation of Intracellular Delivery of the Fusion Protein by Western Blot Analysis>

Figure 3:
FIG. 3 shows the pictures of Western blot analysis confirming that tRORγt-TMD used as one embodiment according to the present invention can be transduced into Jurkat T cells in dose- and time-dependent manner.

We added various concentrations (0, 100 nM, 200 nM, 500 nM, 1 μM, 2 μM, 5 μM) of the fusion protein to the culture medium for Jurakt T cell or C57BL/6 splenocyte for 1 h or incubated these cells with 5 uM of the fusion protein for different lengths of time (0, 1, 3, 4, 12, 24 and 48 h). We then washed with PBS to remove the residual fusion proteins that are not transduced into cells. We confirmed whether tRORγt-TMD is transduced into cells by using mAb recognizing tRORγt-TMD after the proteins in the cell lysates were separated in SDS-PAGE (refer to FIG. 3). We confirmed that tRORγt-TMD was effectively transduced into these cells in a concentration-dependent manner, and most of the fusion proteins were transduced into cells within 1 hour and the transduced proteins started being degraded 48 hours after transduction into cells. Thereby, we expect that there may not be a cytotoxic effect due to the presence of high concentration of the fusion protein for a long time in the cells.

<2-2. Confirmation of the Delivery of the Transduced Fusion Protein into the Nucleus Using mAb>

500 nM of tRORγt-TMD was transduced into HeLa cell for 1 h, and then the cells were washed with PBS and the cell membrane was permeabalized using Triton X-100 in the presence of fluorescence-tagged mAb specific to the fusion protein. Then, we confirmed that the fluorescence of mAb specific to the transduced fusion proteins is overlapped with the nucleus which was stained by DAPI, suggesting that the transduced fusion protein is transported into the nucleus (refer to FIG. 4a).

Figure 4:
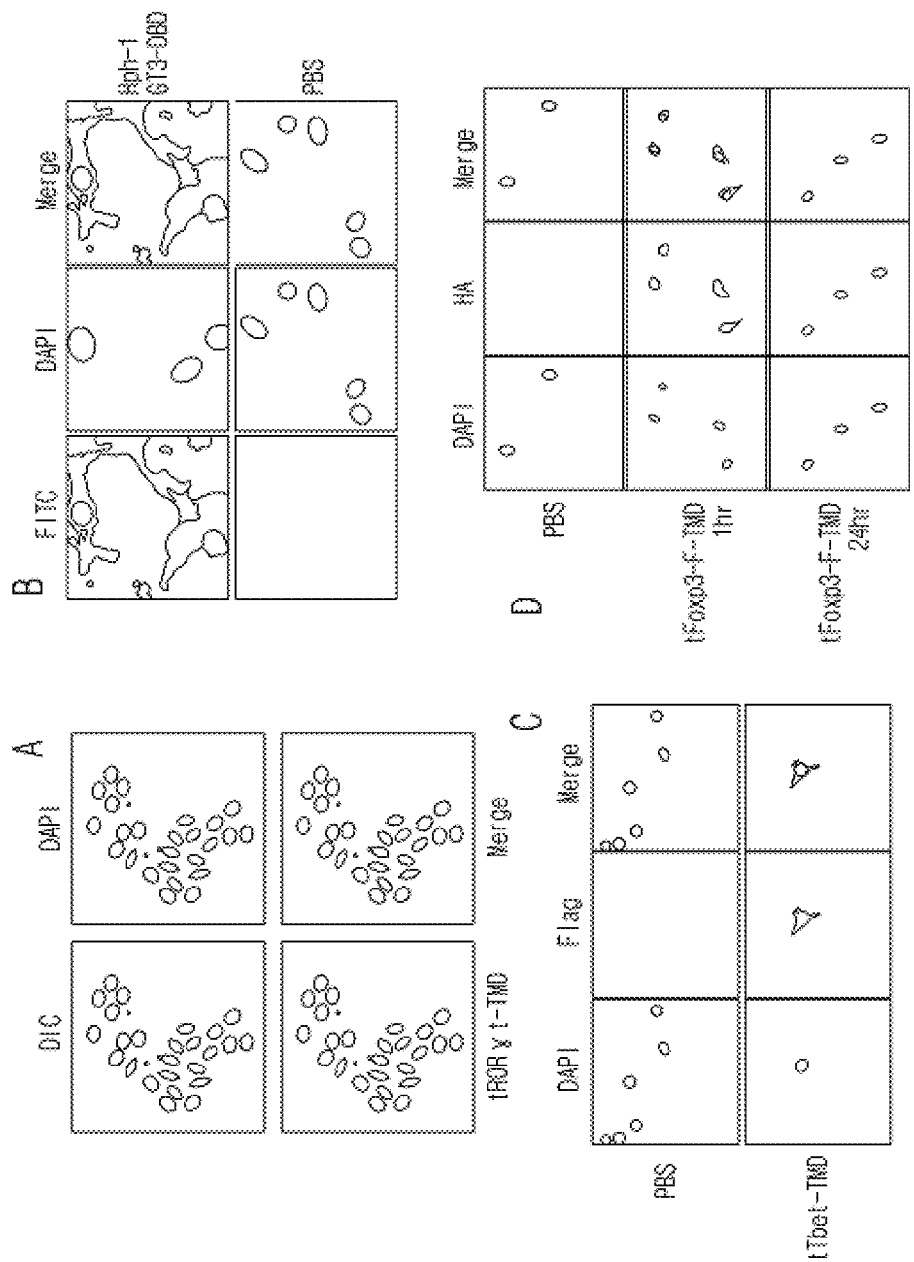
FIG. 4 shows that tRORγt-TMD fusion protein used as one embodiment according to the present invention can be delivered into the nucleus of HeLa cells analyzed by fluorescence microscopy.

Using the same experimental methods described above tGT3-TMD comprising the transcriptional modulation domain of GATA-3 (SEQ ID NO: 3) in FIG. 1, tTbet-TMD comprising the transcriptional modulation domain of Tbet (SEQ ID NO: 4) and tFoxp3-TMD comprising the transcriptional modulation domain of Foxp3 (SEQ ID NO: 5, 6) were effectively transduced into the cells and even into the nucleus of the cells (refers to FIGS. 4b, 4c and 4d).

Example 3

Specific Inhibition of the Transcriptional Activity of the TF by the Fusion Protein <3-1. Inhibition of Secretion of Cytokine IL-17A by tRORγt-TMD>

Figure 5:
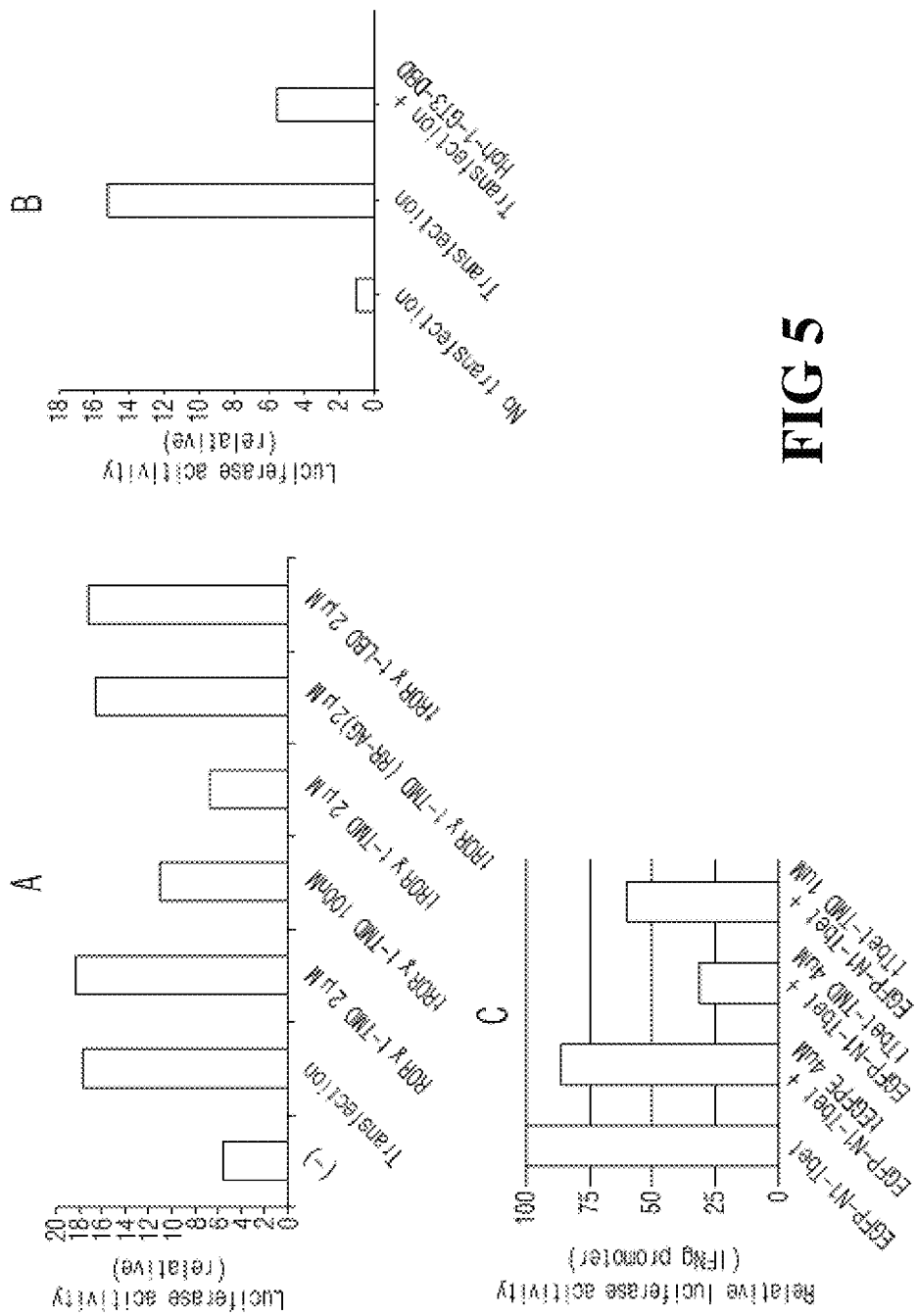
FIG. 5 shows the results that the tRORγt-TMD inhibits the DNA binding activity of the endogenous RORγt to the IL-17 promoter in a concentration-dependent manner while tRORγt-LBD, RORγt-TMD that does not have Hph-1-PTD or the mutant form of tRORγt-TMD (RR-AG) that cannot bind to IL-17 promoter due to the mutations in amino acids critical in DNA binding cannot inhibit the DNA binding activity of the endogenous RORγt.

To test whether tRORγt-TMD is able to inhibit competitively and specifically the binding of the endogenous tRORγt to the promoter region of IL-17, Hela cells were transfected with the DNA expressing tRORγt and the luciferase reporter DNA whose expression is driven by IL-17 promoter together, and incubated with tRORγt-TMD. We used lipofectamine to transfect Hela cells with DNAs. The mixture of the plus reagent (Invitrogen), 1 μg of luciferase reporter construct and 1 μg pRORγt-N1 plasmid was diluted to the appropriated volume with Opti-MEM (Gibco) in the absence of serum. After leaving the trasfection mixture in room temperature for 15 minutes to make the complex, Hela cells (1×105 cells per well) were mixed with DNA-Plus-Lipofectamine Reagent complex for 3 hours, and then treated with 100 nM-2 μM of tRORγt-TMD, tRORγt-LBD or non-transducible RORγt-TMD fusion proteins overnight. We measured luciferase activity using a luciferase detection system (Promega) after washing and extraction. Each transfection experiment was performed three times and the activity of luciferase was tested by luminator (Promega). tRORγt-TMD fusion protein reduced luciferase activity by 6 folds, whereas tRORγt-LBD or non-transducible RORγt-TMD didn't affect it. In addition, the mutant form of tRORγt-TMD (RR-AG) which cannot bind to DNA by mutation of amino acids critical for DNA binding couldn't prevent luciferase activity because the mutant form was not able to bind to IL-17 promoter (FIG. 5). Therefore, tRORγt-t-TMD fusion protein specifically inhibits the binding of endogenous RORγt to IL-17 promoter and this inhibitive function was specific to IL-17 promoter.

Using the same experimental methods as described above, inhibition of luciferase activity by tGT3-TMD comprising the transcriptional modulation domain of GATA-3 and tTbet-TMD comprising the transcriptional modulation domain (SEQ ID NO: 4) was confirmed (refer to FIGS. 4b and 4c).

We isolated the splenocytes from the spleens of 7-week-old female C57BL/6 mice and then measured the amount of cytokines secreted from Th1, Th2 or Th17 cells by ELISA after incubating the splenocytes in 12 wells which were coated with 1 μg/ml of anti-CD3 antibody and 0.5 μg/ml of anti-CD28 antibody for 72 hours. We figured out that the increase of IL-2 secretion, which indicates the T cell activation, of that of IFN-γ which represents Th1-specific cytokine, that of IL-4 which represents Th2-specific cytokine, and that of IL-17A which represents Th17-specific cytokine was induced by TCR stimulation through both anti-CD3 and anti-CD28 antibodies.

Figure 6:
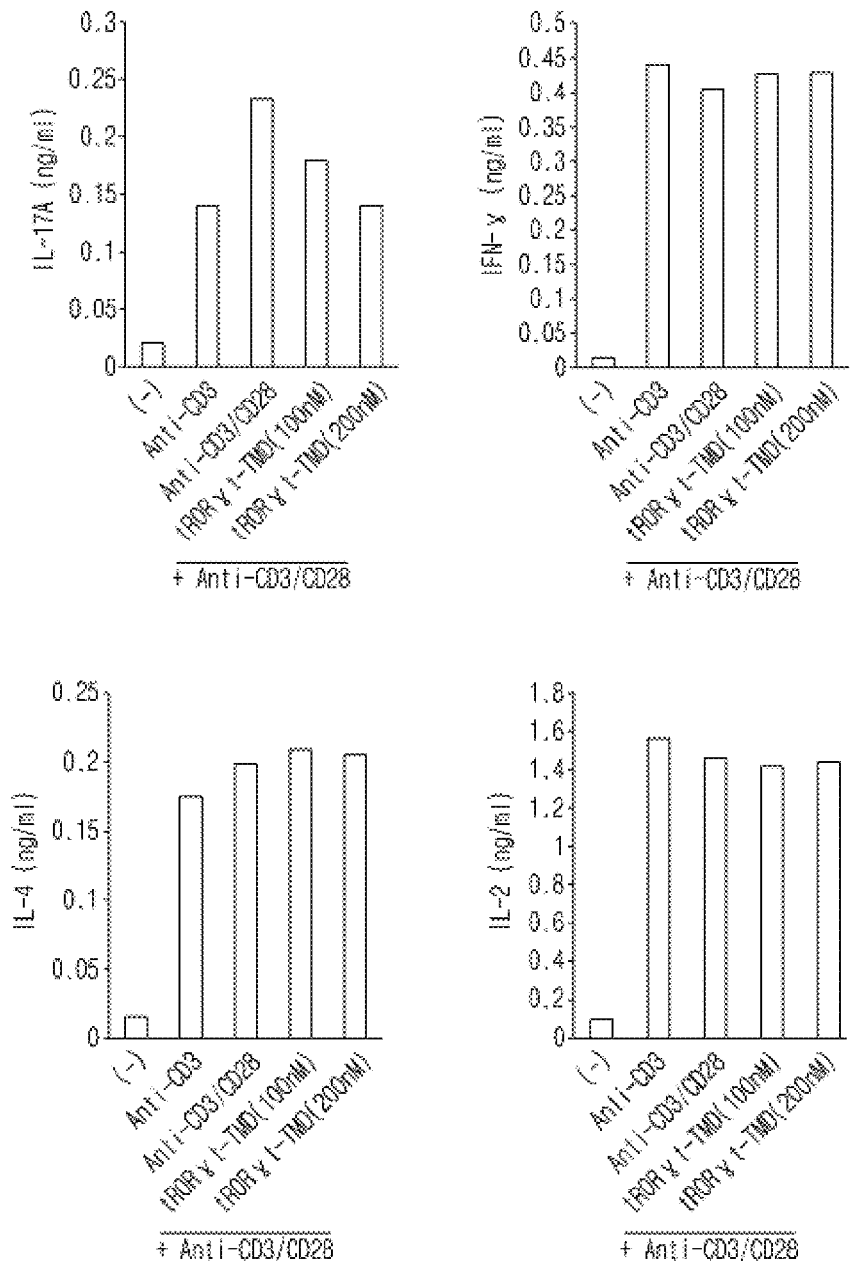
FIG. 6 shows the results that tRORγt-TMD fusion protein used as one embodiment according to the present invention selectively inhibits the secretion of IL-17A from Th17 cells in splenic T cells upon TcR activation induced by anti-CD3 and anti-CD28 mAb, but does not affect the secretion of IFN-γ from Th1 cells, secretion of IL-4 from Th2 cells or the secretion of IL-2 from the activated T cells.

To confirm whether tRORγt-TMD fusion protein can suppress the function of endogenous RORγt which induces the expression and secretion of IL-17A from Th17 cells, we incubated splenocytes with 200 nM of tRORγt-TMD fusion protein for 1 hour in advance and then the cells were washed to remove the un-transduced tRORγt-TMD. As described above, the cells were stimulated by anti-CD3 and anti-CD28 antibodies and the level of cytokine secretion was analyzed. As a result, the level of secretion of IFN-γ, IL-4 or IL-2 was not changed by transduction of tRORγt-TMD into the cells, whereas that of IL-17A was decreased in a dose-dependent manner. From these results, tRORγt-TMD specifically inhibits the secretion of Il-17A from Th17 cells, but does not affect the secretion of IFN-γ from Th1 cells, secretion of IL-4 from Th2 cells and IL-2 secretion from the activated T cells (refer to FIG. 6).

<3-2. Selective Inhibition of Differentiation of Naive T Cells into Th17 Cells by tRORγt-TMD>

Figure 7:
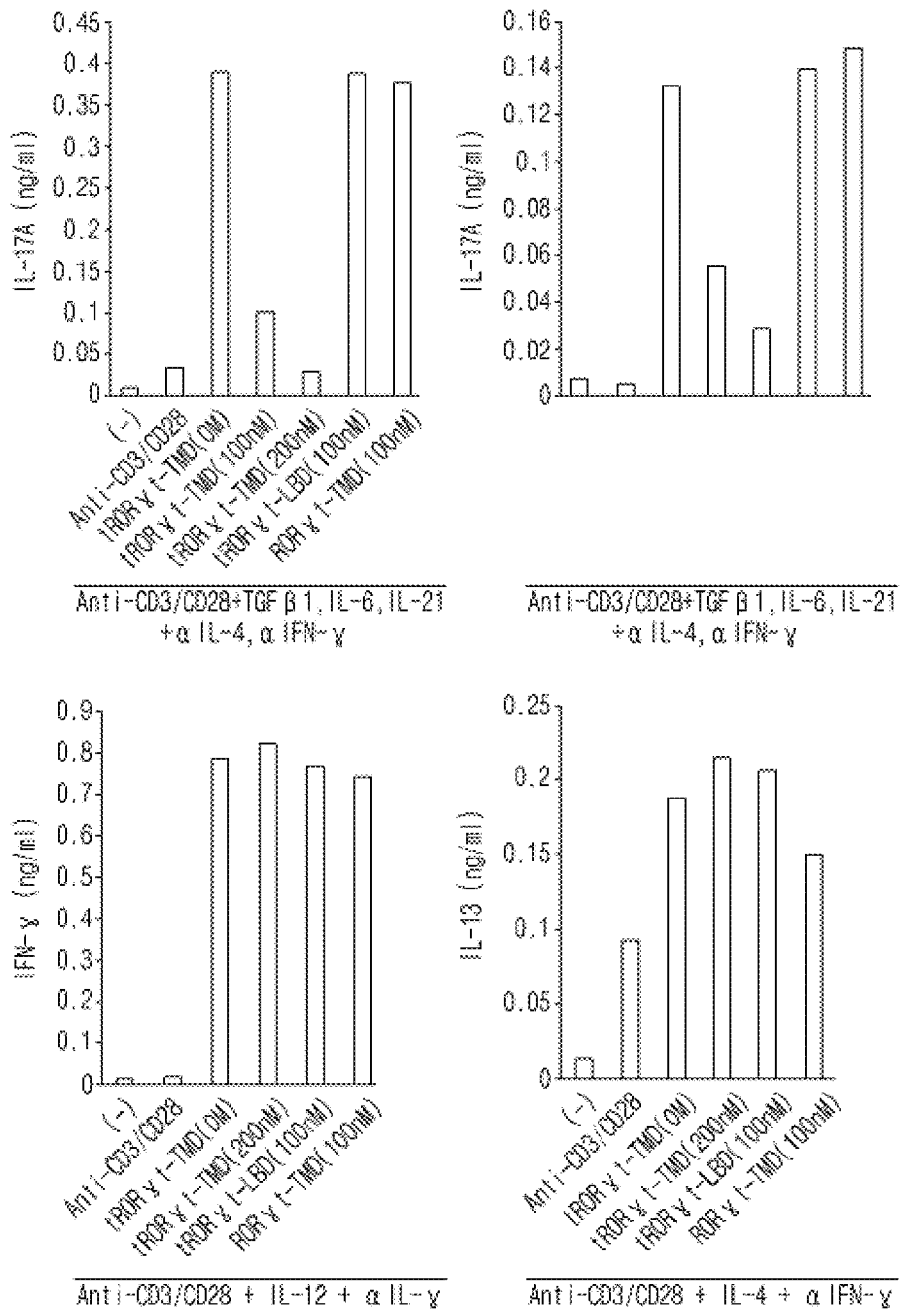
FIG. 7 shows that tRORγt-TMD fusion protein used as one embodiment according to the present invention selectively inhibits the differentiation CD4+CD25−CD62L+naive T cells into Th17 cells and the expression and secretion of IL-17A and IL-17F from Th17 cells. However, tRORγt-TMD does not affect the differentiation of CD4+CD25−CD62L+naive T cells into Th1 cells and the expression and secretion of IFN-g from Th1 cells and the differentiation of CD4+CD25−CD62L+naive T cells into Th2 cells and the expression and secretion of IL-13 from Th2 cells. And, tRORγt-LBD and RORγt-TMD that does not have Hph-1-PTD do not inhibit the differentiation of CD4+CD25−CD62L+naive T cells into Th17 cells. In addition, the tRORγt-TMD (RR-AG) that has mutations of tRORγt-TMD in the amino acid involved in DNA binding can partially inhibit the secretion of IL-17A from TH17 cells.

With the same protocol mentioned in experiment 3-1, immature naive CD4+CD25-CD62L T cells from the spleen of 7-week-old female C57BL/6 mice using MACS (Magnetic Cell Sorting) were isolated and these cells have never encountered any antigens previously. After treating these immature and naive CD4 T cells with 100 nM or 100 fM of tRORγt-TMD for 1 hour, we incubated the cells with the cytokines which can induce the differentiation of naive T cells into Th1, Th2 or Th17 cells together with TcR stimulation by 1 μg/ml of anti-CD3 antibody and 0.5 μg/ml of anti-CD28 antibody for 72 hours. We added 10 ng/ml of IL-12 and anti-IL-4 antibody to differentiate T cells into Th1 cell. We added IL-4, IL-5 ng/ml and anti-IFN-r antibody to differentiate naive T cells into Th2 cell, and 3 ng/ml of TGFβ1, 30 ng/ml of IL-6, 100 ng/ml of IL-21, anti-IL-4 antibody, and anti-IFN-γ antibody to induce the differentiation of naive T cells into Th17. When the level of cytokines secreted into the cell supernatant was analyzed by ELISA after 72 hours of incubation, Th1-specific and Th2-specific cytokines were not changed, whereas Th17 cell-specific cytokines such as IL-17A and IL-17F which are known to be induced by RORγt were decreased significantly. From these results, tRORγt-TMD can selectively inhibit the differentiation of naive T cells into Th17 cells and expression and secretion of Th17 cell-specific cytokines in which RORγt plays crucial roles (refer to FIG. 7).

Figure 8:
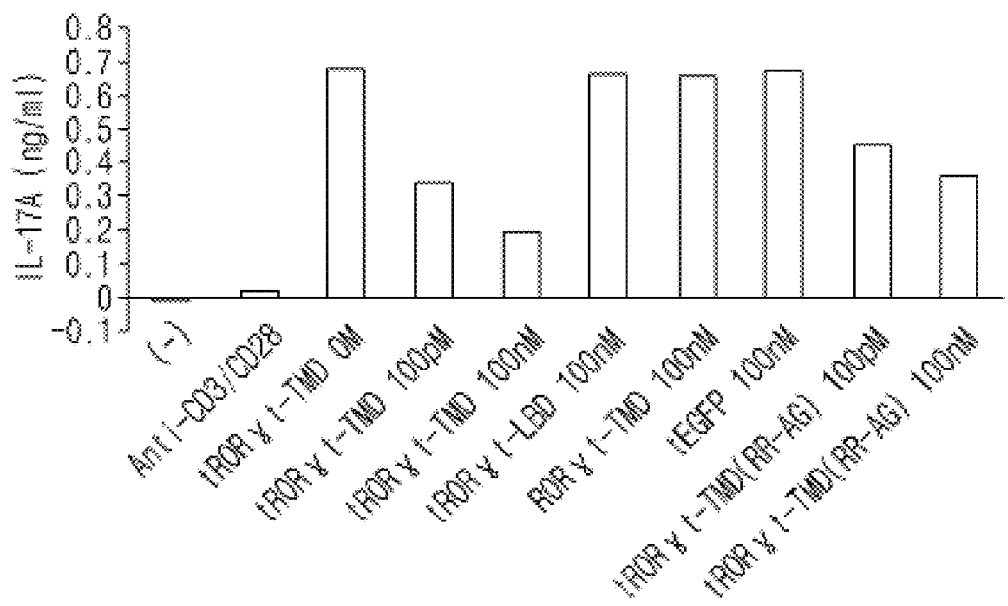
FIG. 8 shows the results that tRORγt-TMD inhibits tRORγt present in the cell from binding to IL-17A promoter in a concentration-dependent manner; and the inhibition effect is not observed in the fusion protein with LBD (tRORγt-LBD) and RORγt-TMD without PTD, but the mutant form of tRORγt-TMD (RR-AG), which cannot bind to DNA due to the mutation of amino acid involved in the binding with DNA, partially inhibits the IL-17A from Th17 cells.

Next, we investigated whether the binding of tRORγt-TMD to the regulatory region of the genes whose expression is induced by RORγt is important for the inhibition of the differentiation of naive T cells into Th17 cells by tRORγt-TMD. Under the same experimental condition as described above, we treated the naive T cells with tRORγt-TMD (RR-AG) in which the amino acids critical for DNA binding of tRORγt-TMD were mutated, instead of tRORγt-TMD. tRORγt-TMD (RR-AG) couldn't bind to IL-17 gene promoter which is induced by RORγt, whereas the differentiation of naive T cells into Th17 cell was partially inhibited. From this result, tRORγt-TMD could not only prevent the endogenous RORγt from binding to the promoter of the genes induced by RORγt, but also inhibited the function of interactome recruited by RORγt in the promoter of RORγt-induced genes, thereby inhibiting the differentiation of naive T cells into Th17 cells (refer to FIG. 8).

To confirm the modulatory function of ligand-binding domain in RORγt carboxyl terminal in the differentiation of naive T cells into Th17 cells, we performed an experiment with the same protocol as described above in <3-2> except treating the naive T cells with 100 nM of tRORγt-LBD instead of tRORγt-TMD. As a result, tRORγt-LBD does not affect the differentiation of naive T cells into Th1, Th2, or Th17 cells. From the result, we confirmed that only tRORγt-TMD can specifically inhibit the differentiation of naive T cells into Th17 cells since ROTγt-TMD without PTD is not delivered into the cells.

<Inhibition of Differentiation of Naive T Cells into Th1 Cells>

To investigate whether tTbet-TMD can inhibit the differentiation of naive T cells into Th1 cells, we prepared the spleens, isolated the naive CD4+CD62L T cells from the spleens of 7-week-old female C57BL/6 mice using MACS (Magnetic Cell Sorting) and treated these cells with 4 uM of ttTbet-TMD for 2 hours. After washing the cells to eliminate the un-transduced tTbet-TMD protein, the cells were cultured in the presence of IL-12 (10 ng/ml) and anti-IL-4 (5 ug/ml) following TcR stimulation with anti-CD3 mAb (1 ug) and anti-CD28 mAb (1 ug) for 72 hours, and the cells were harvested and restimulated with PMA (50 ng/ml) and ionomycin (1 ug/ml) for 4 hours. The cells were permeabalized, incubated with anti-IFN-g mAb labeled with FITC and then the level of intracellular IFN-g was analyzed by FACS. From this result the naive T cells treated with tTbet-TMD could not be differentiated into Th1 cells, suggesting that tTbet-TMD suppresses the functions of the endogenous Tbet, leading to the inhibition of differentiation of naive T cells into Th1 cells and functions of Th1 cells. Therefore, tTbet-TMD can be a novel therapeutic to alleviate chronic inflammatory responses and autoimmune diseases in which Th1 cells play dominant roles.

<Functional Inhibition of Natural Regulatory T Cells>

Figure 9:
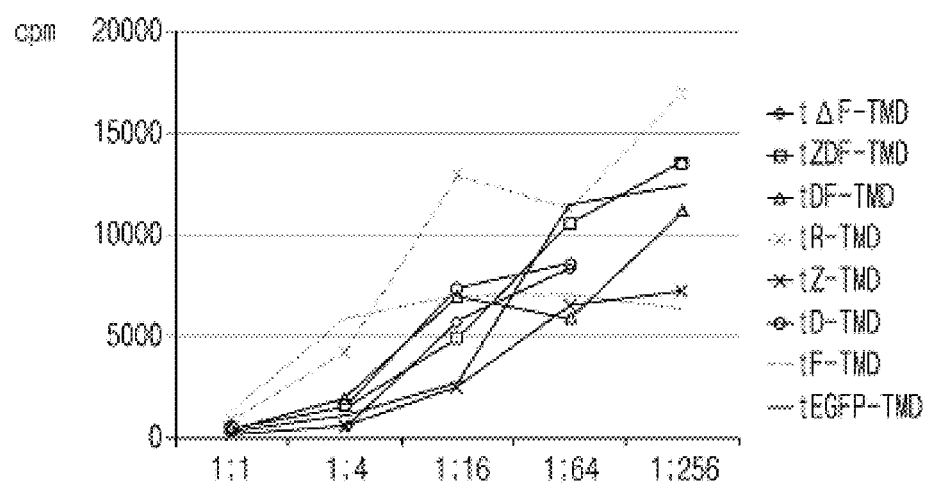
FIG. 9 shows the results that upon intracellular delivery of tFoxp3-TMD into nTreg cells, tFoxp3-TMD fusion protein, which is used as one embodiment in the present invention, effectively reduces the immunological suppressive functions of nTreg cells on effector T cells through interactomic competition of endogenous Foxp3.
Figure 9:
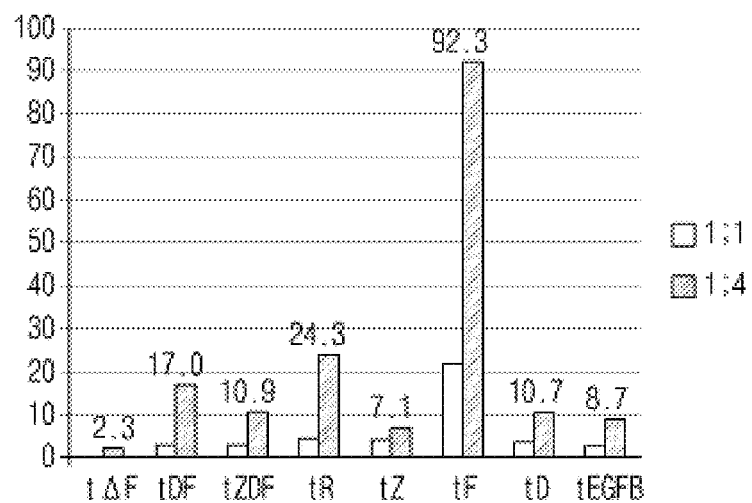

We next investigated whether tFoxp3-TMD can suppress the immunological functions of nTreg cells via competitive inhibition of the endogenous Foxp3 in nTreg cells. We prepared the spleens, isolated nTreg cells from the spleens of 7-week-old female C57BL/6 mice using MACS (Magnetic Cell Sorting), stimulated the proliferation of nTreg cells using BMDC (Bone Marrow Dendritic Cells) expressing allogeneic MHC and then treated these cells with tFoxp3-TMD. nTreg cells treated with tFoxp3-TMD were co-cultured for 72 hours with CD4+CD25-T cells prepared as the effector T cells, and immunosuppressive potential of nTreg cells on effector T cells was analyzed by the method of thymidine incorporation into effector T cells. These results demonstrated that nTreg cells treated with all tFoxp3-TMD except tFoxp3-F-TMD showed a similar level of immunosuppressive activity on effector T cells proliferation, and especially nTreg cells treated with tFoxp3-F-TMD from 1:4 ratio of nTreg cells to effector T cells showed the most prominent immunosuppression on proliferation of effector T cells. These results suggest that the amino acid residues in tFoxp3-F-TMD involved in recognition of DNA sequences inhibit the functions of the endogenous Foxp3 or/and tFoxp3-F-TMD may inhibit the functions of transcription co-activators making an access to the promoter region of the genes induced by endogenous Foxp3, thereby suppressing the functions of nTreg cells (FIG. 9)

<Functional Inhibition of Induced Regulatory T Cells (iTreg)>

We next investigated whether tFoxp3-TMD comprising the different functional TMD can suppress the immunological functions of iTreg cells via competitive inhibition of the endogenous Foxp3 in iTreg cells. We prepared CD4+ T cells from the splenocytes of FoxP3-GRP-Knock-In (KI) mouse using MACS, and further purified CD4+GFP-CD62L2+ cells using FACS. These cells were treated with tFoxp3-TMD and induced to differentiate into iTreg cells by culturing them in the presence of TGF (10 ng/ml) and IL-2 (100 U/ml) following TcR stimulation via anti-CD3 and anti-CD28 mAb for 72 hours. Then, the immunosuppressive activity of iTreg cells treated with tFoxp3-TMD on proliferation and functions of effector T cells was analyzed by the method of thymidine incorporation into effector T cells. The level of Foxp3 expression was comparable between iTreg cells differentiated from naive T cells treated with tFoxp3-F-TMD and those from naive T cells without tFoxp3-F-TMD treatment. These results demonstrated that iTreg cells treated with all tFoxp3-TMD except tFoxp3-F-TMD and tFoxp3-R-TMD showed a comparable level of immunosuppressive activity on effector T cells proliferation, but iTreg cells treated with tFoxp3-F-TMD or tFoxp3-R-TMD from 1:4 ratio of nTreg cells to effector T cells showed the most prominent immunosuppression on proliferation of effector T cells. These results suggest that the amino acid residues in tFoxp3-F-TMD involved in recognition of DNA sequences inhibit the functions of the endogenous Foxp3, and/or tFoxp3-F-TMD may inhibit the functions of transcription co-activators making an access to the promoter region of the genes induced by endogenous Foxp3, thereby suppressing the functions of iTreg cells. And, the result that immunosuppressive potential of iTreg cells on effector T cells can be inhibited upon treatment of iTreg cells with tFoxp3-R-TMD comprising the R (repressor) domain instead of the F (Forkhead binding) domain demonstrates that tFoxp3-R-TMD effectively inhibits the transcriptional activity and functions of the endogenous Foxp3 in iTreg cells independent of DNA binding.

Figure 10:
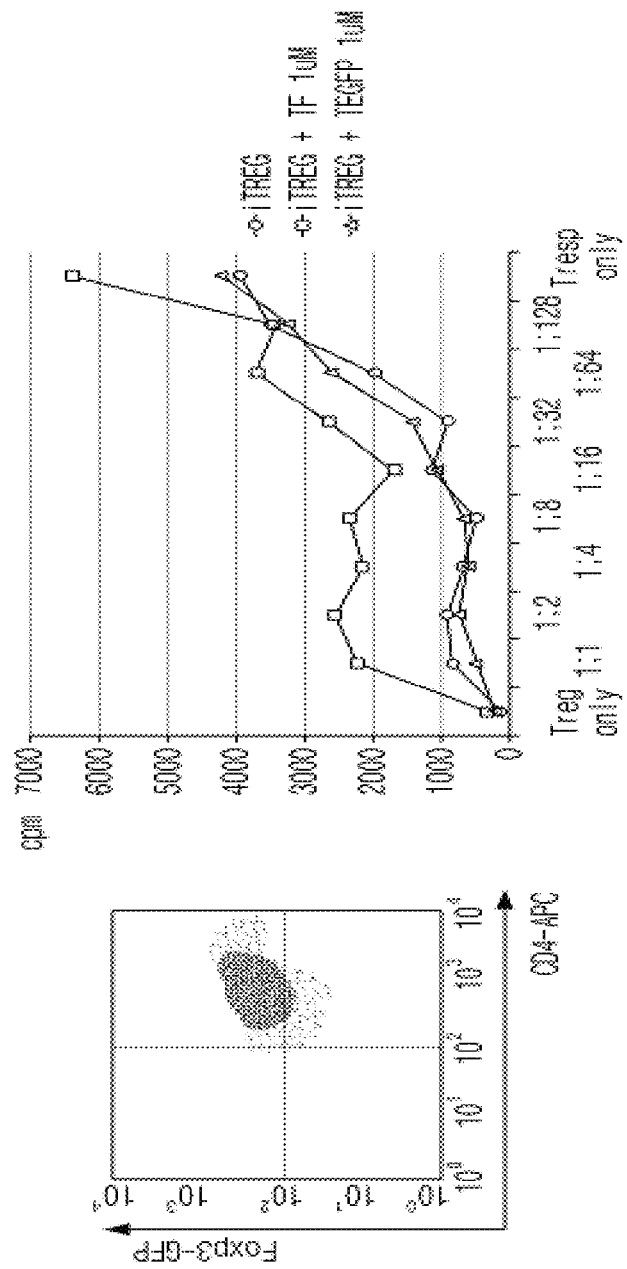
FIG. 10 shows a bar graph displaying the results of FIG. 9.

However, iTreg cells treated with other tFoxp3-TMDs could not reduce the immunosuppressive functions of iTreg cells on effector T cells. Therefore, the amino acid residues in tFoxp3-F-TMD involved in recognition of DNA sequences inhibit the functions of the endogenous Foxp3 and/or tFoxp3-F-TMD may inhibit the functions of transcription co-activators making an access to the promoter region of the genes induced by endogenous Foxp3, thereby suppressing the functions of nTreg cells and iTreg cells (FIG. 10).

Example 4

Therapeutic Efficacy of tRORγt-TMD Fusion Protein in EAE Animal Model

<4-1. Analysis of Therapeutic Efficacy of tRORγt-TMD in EAE Animal Model>

To analyze the therapeutic efficacy of tRORγt-TMD in EAE (the animal model of human MS) where Th17 cells play an important role, EAE animal model was generated with 6-week-old C57BL/6 mice. The mice had 2 weeks of stabilization period, and 500 ng of Pertussis Toxin was injected into the abdominal cavity of the mice followed by injection of 150 ng of MOG peptide and 200 ug of CFA into the subcutaneous fat. In general, the behavioral responses started from the 9th day of post-injection. The first was paralysis of the tail, and then that of the hind legs, and forelimb paralysis appeared at the severe disease stage. Each symptom was scored for evaluation of disease progression (1 point: slight paralysis of the tail, 2 points: complete paralysis of the tail and slight paralysis of the hind legs, 3 points: complete paralysis of one hind leg, 4 points: complete paralysis of both hind legs, 5 points: complete paralysis of both hind legs and slight paralysis of the forelegs, 6 points: death). 50 μg of tRORγt-TMD was injected into the peritoneal cavity three times a week from the 2nd day of disease induction. The results indicate that the disease onset frequency was reduced by 50% in the mice treated with tRORγt-TMD and the disease severity was improved to be minimal. The disease onset frequency of the untreated mice was 100% and the disease severity was 3.05±0.23, but that of the mice treated with tRORγt-TMD was 0.55±0.27. These results demonstrate that tRORγt-TMD has a marked disease prevention effect on EAE (animal model of MS) where Th17 cells play a critical role.

Figure 11:
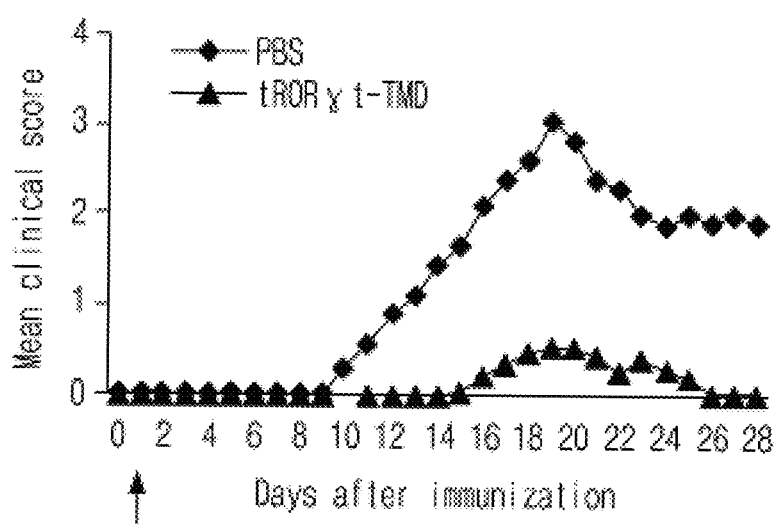
FIG. 11 shows that tRORγt-TMD fusion protein used as one embodiment in the present invention has an effective therapeutic and preventive potential on EAE which is the animal model of human multiple sclerosis (MS).
Figure 11:
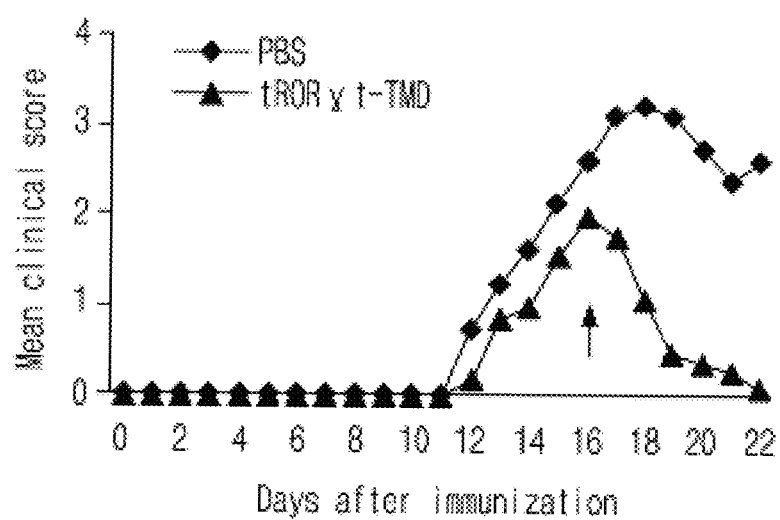

To investigate the therapeutic efficacy of tRORγt-TMD on Th17 cell-mediated induction and maintenance of EAE, 50 ug of tRORγt-TMD started being injected three times a week into the peritoneal cavity of the mice with EAE in which the disease symptoms progressed into complete paralysis of one hind leg, clinical score 3. The EAE clinical score significantly dropped down right after tRORγt-TMD injection, and the EAE symptoms almost completely disappeared on the 22nd day. Therefore, tRORγt-TMD has a preventive and therapeutic effect on EAE autoimmunity mainly induced by Th17 cells (FIG. 11).

<4-2. Cellular Mechanisms of Action of tRORγt-TMD on EAE with Regard to Therapeutic Effectiveness>

Figure 12:
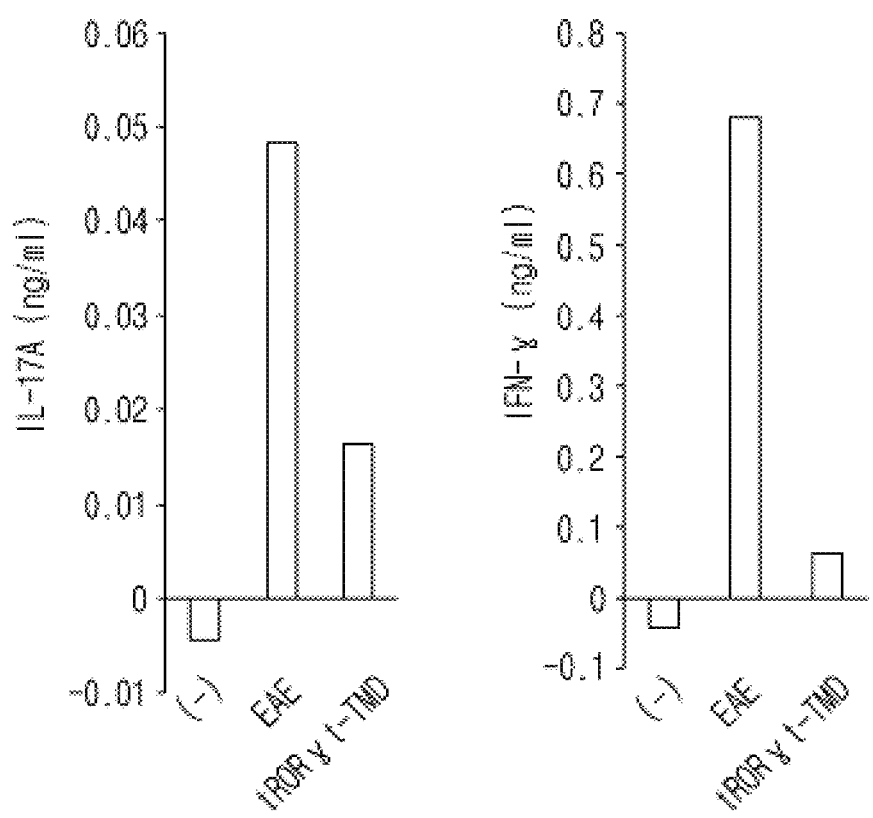
FIG. 12 shows that tRORγt-TMD fusion protein used as one embodiment in the present invention inhibits the differentiation of naive T cells into Th17 cells and secretion of IL-17A from Th17 cells, and this inhibitory activity of tRORγt-TMD can also inhibit the secretion of IFN-g from Th1 cells, which are analyzed by ELISA.
Figure 13:
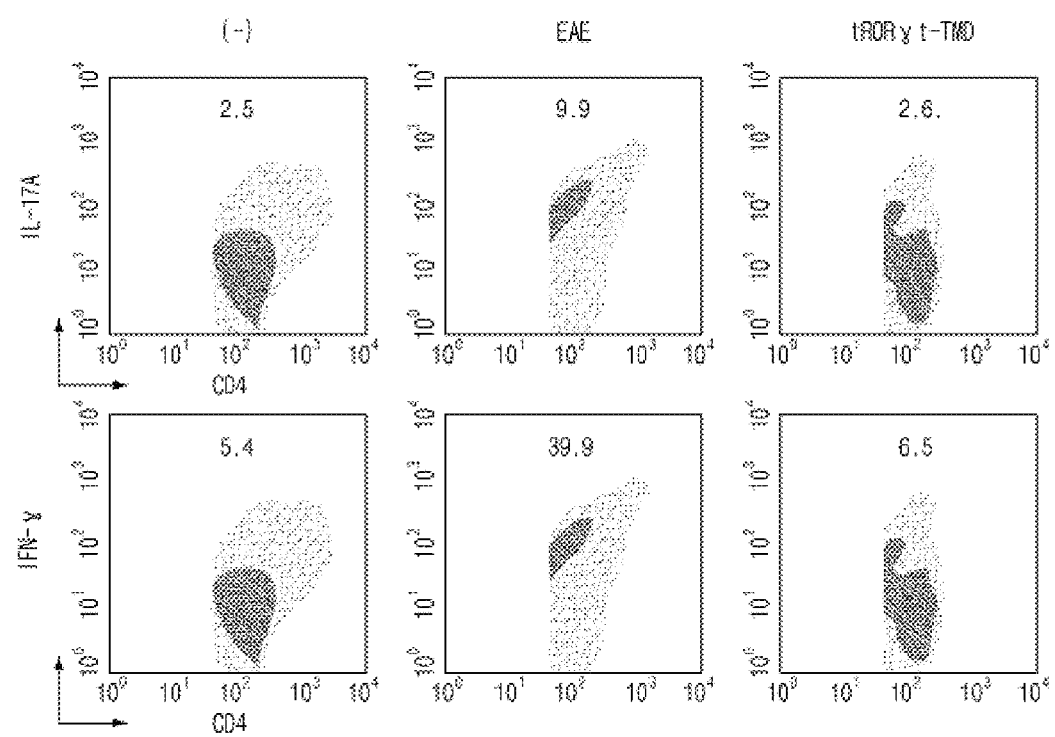
FIG. 13 shows that tRORγt-TMD fusion protein used as one embodiment in the present invention inhibits the differentiation of naive T cells into Th17 cells and secretion of IL-17A from Th17 cells, and this inhibitory activity of tRORγt-TMD can also inhibit the secretion of IFN-g from Th1 cells, which are analyzed by intracellular staining.

CD4+ T cells isolated from the spleen of the mice with EAE showing the therapeutic efficacy by tRORγt-TMD were prepared and re-stimulated with the antigenic peptide MOG which was used to induce EAE. The CD4+ T cells in the mice had differentiated into the specific CD4+ T cell subset upon recognition of MOG peptides and thereby the differentiated CD4+ T cells can secrete the cytokines specific to the T cells subset when re-stimulated with the same antigenic peptide. On the 10th day of post-EAE induction, splenocytes were prepared from the mice treated with tRORγt-TMD from 2 days after EAE induction, and re-stimulated with 40 μg/ml of MOG peptide for 48 hours. When the level of cytokines in the culture supernatant of the splenocytes was analyzed by ELISA, IL-17A cytokine secretion from Th17 cells as well as IGN-g from Th1 cells were significantly reduced (FIG. 12). Similar results were obtained from the experiment in which the splenocytes were treated with Golgi PLUG to prevent the cytokine secretion, and the level of intracellular cytokine was analyzed by intracellular staining and FACS using the fluorescence-labeled mAb specific to each cytokine (FIG. 13). Therefore, the preventive and therapeutic effect of tRORγt-TMD on EAE is due to the specific functional inhibition of the endogenous RORγt and the suppression of differentiation and functions of Th17 cells, leading to the inhibition of cytokine secretion such as IL-17 from Th17 cells. The fact that inhibition of Th17 cell differentiation and functions via RORγt can lead to inhibition of Th1 cytokine secretion such as IFN-g suggests that Th17 cells may be activated and play dominant functions during the initial stage of EAE followed by the activation and functions of Th1 cells later.

<4-3. Histological Analysis of Therapeutic Effectiveness on EAE by tRORγt-TMD>

Figure 14:
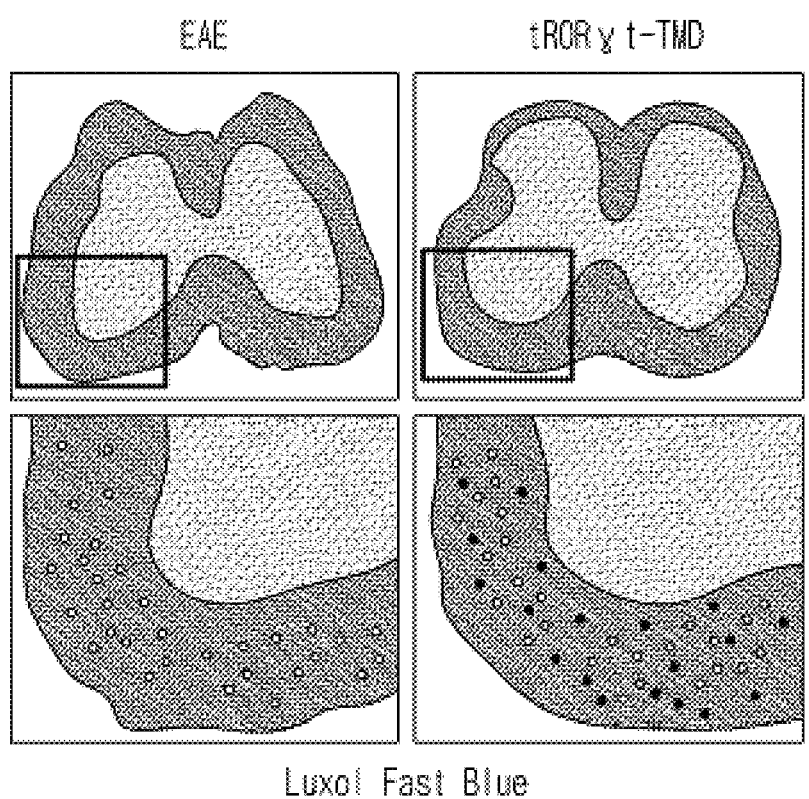
FIG. 14 shows that tRORγt-TMD fusion protein used as one embodiment in the present invention can exert the inhibitory effect on demyelination of neuron cells in CNS in EAE, animal model of human MS through Luxol Fast Blue staining that can stain the myelinated area.
Figure 15:
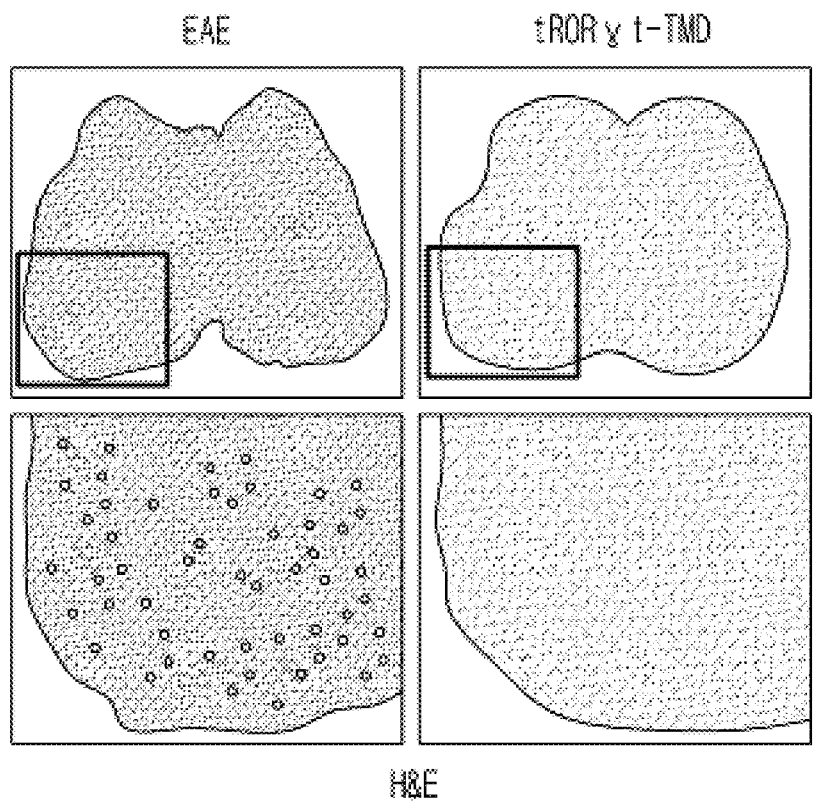
FIG. 15 shows the picture that tRORγt-TMD fusion protein used as one embodiment in the present invention inhibits the infiltration of inflammatory cells into CNS in EAE, animal model of human MS through Hematoxylin & Eosin immunohistochemical staining.
Figure 16:
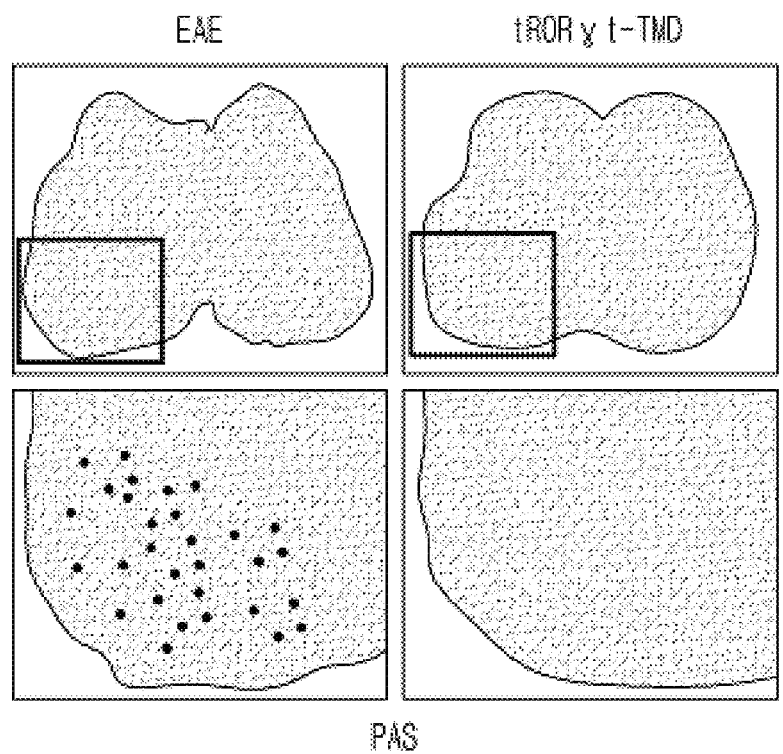
FIG. 16 shows the picture that tRORγt-TMD fusion protein used as one embodiment in the present invention inhibits the infiltration of inflammatory cells into CNS in EAE, animal model of human MS through Periodic acid Schiff immunohistochemical staining.

To make the histological analysis of therapeutic effectiveness of tRORγt-TMD on EAE, the spinal cords of the mice were harvested on day 21 when the EAE clinical score was highest in the untreated mice, and the level of demyelination was examined. Luxol Fast Blue was used to stain the myelinated tissue area so that the tissue with severe demyelination at the late stage of EAE cannot be stained. The myelination state of the spinal cord of the EAE-induced mice treated with tRORγt-TMD was similar to that of the normal mice. When the extent of inflammatory cell infiltration was examined by H&E and PAS staining, severe infiltration of inflammatory cells into the spinal cord was observed in EAE-induced mice, but tRORγt-TMD treatment on EAE-induced mice did not show any noticeable level of inflammatory cell infiltration into the spinal cords. Taking all these results together, tRORγt-TMD exerts therapeutic efficacy on EAE by inhibition of the functions of the endogenous RORγt leading to the suppression of the differentiation of naive T cells into Th17 cells and functions of Th17 cells such as secretion of IL-17 in vitro and in vivo (FIGS. 14, 15 and 16).

Example 5

Therapeutic Effect of tGT3-TMD on Allergic Asthma

<5-1. Cellular Analysis of Therapeutic Efficacy of tGT3-TMD on Allergic Asthma>

Figure 17:
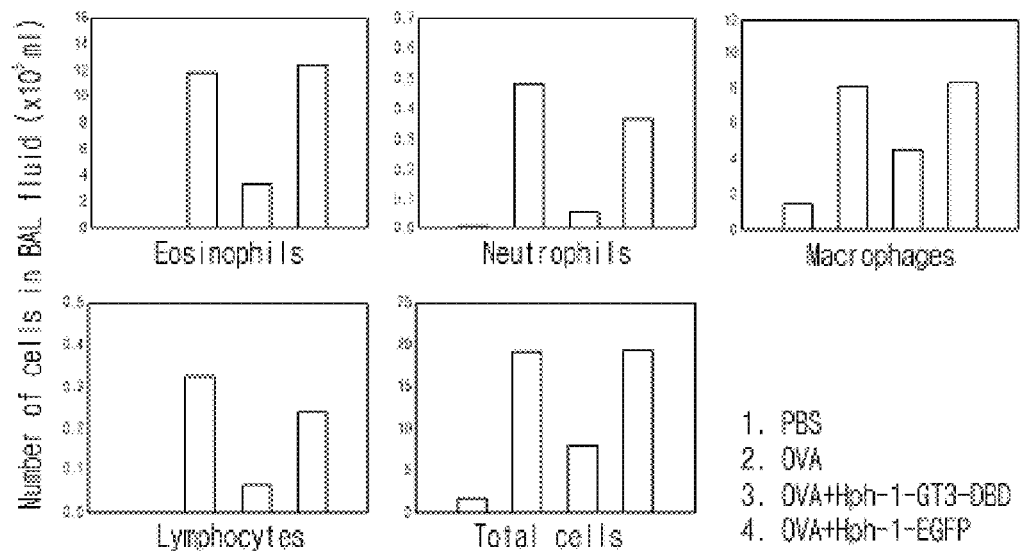
FIG. 17 shows the graph that tGT3-TMD fusion protein used as one embodiment in the present invention can decrease the infiltration of several different inflammatory and immune cells effectively when tGT-PTMD is intranasally sprayed into the airway in the animal model of allergic asthma which is analyzed by the cell differential staining.
Figure 18:
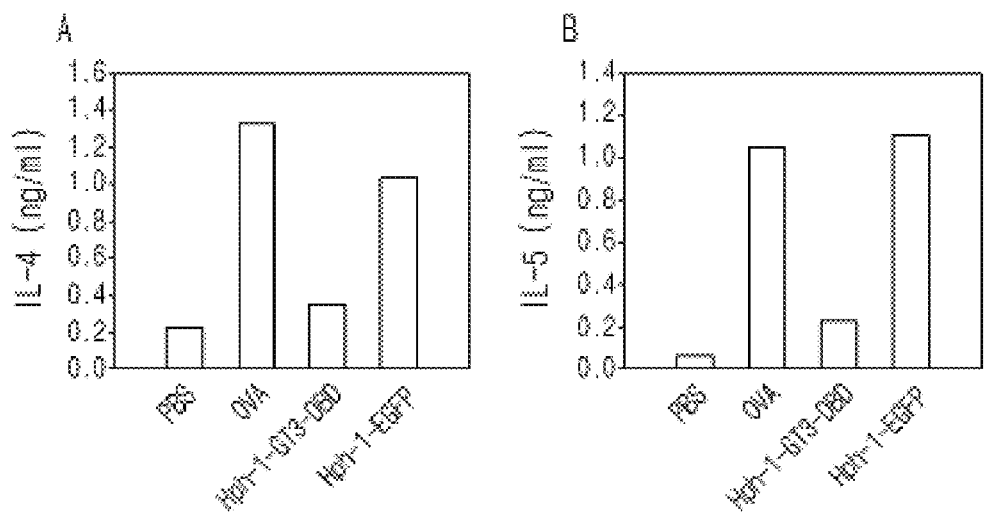
FIG. 18 shows the graph that tGT3-TMD fusion protein used as one embodiment in the present invention has a therapeutic effect in the animal model of allergic asthma by inhibiting the secretion of Th2-specific cytokine IL-4 and IL-5 when tGT3-TMD is intranasally sprayed into the airway, which is analyzed by ELISA.

To investigate the in vivo therapeutic efficacy of tGT3-TMD on allergic asthma induced by Th2 cells, the animal model of allergic asthma was generated by injection of 100 ug of OVA and 20 mg of aluminum hydroxide into the peritoneal cavity of 6-week-old BALB/c mice at day 1 and day 14. And, 75 ug of tGT3-TMD was sprayed into the intranasal pathway on the 21st, 22nd and 23rd days to deliver tGT3-TMD into the lungs and bronchial space, and 150 ug of OVA was used for the antigenic challenge. On the 25th day of post-injection, the cells were harvested from the BAL fluid and the number of various inflammatory and immune cells was counted. tGT3-TMD treatment significantly reduced the number of various inflammatory and immune cells (FIG. 17). And, the splenic T cells were prepared from the animal model of allergic asthma which showed the therapeutic effect by tGT3-TMD treatment and restimulated with anti-CD3 and anti-CD28. Because these splenic T cells were exposed to OVA antigen in vivo, Th2 cell-specific cytokines can be secreted upon antigenic rechallenge in vitro. When the level of Th2-specific cytokines in the culture supernatant was examined by ELISA, the secretion of IL-2, IL-5 and IL-13 was significantly reduced in mice treated with tGT3-TMD (FIG. 18).

<5-2. Histological Analysis of Therapeutic Effectiveness of tGT3-TMD on Allergic Asthma>

Figure 19:
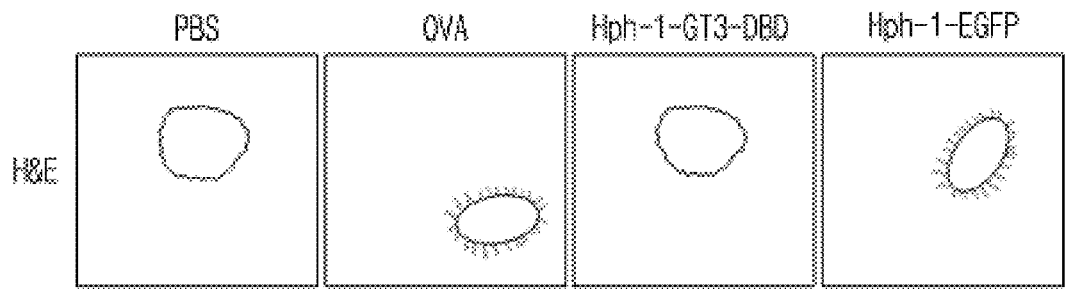
FIG. 19 shows the picture that tGT3-TMD fusion protein used as a specific example in this invention has a therapeutic effect in the animal model of allergic asthma by inhibition of infiltration of several different inflammatory and immune cells effectively, which is analyzed by Hematoxylin & Eosin staining.

To make the histological analysis of the therapeutic efficacy of tGT3-TMD on the severity of lung and brochial inflammation by immunohistochemical method, the animal model of OVA-induced allergic asthma was treated with tGT3-TMD, the lung and brochial tissues were kept in formaldehyde solution for 24 hours following the washing with PBS and the elimination of RBC, and paraffin tissue sections were prepared. When these paraffin tissue sections were stained with H&E and PAS, the histological status of lung and bronchial tissues from the mice treated with tGT3-TMD was close to normal in comparison with those from the untreated mice where severe tissue destruction was observed. And, the extent of inflammatory cell infiltration was significantly reduced. On the basis of these results, it is suggested that tGT3-TMD inhibits the functions of the endogenous GATA-3 and suppresses immunological functions of Th2 cells, leading to therapeutic effectiveness on allergic asthma (FIG. 19).

Example 6

Analysis of Acute Toxicity of tRORγt-TMD or tGT3-TMD

Acute toxicity test was performed with 6-week-old specific pathogen free (SPF) SD rats which were supplied from the Korean Experimental Distribution Center.

After two rats per each experimental group were treated once with 1 g/kg of tRORγt-TMD or tGT3-TMD mortality, clinical symptoms and body weight change were monitored, hematological and blood biochemical tests were carried out, and the visual examination of the abnormality of each organ and lung was performed upon autopsy.

The clinical abnormality and mortality was not observed in the rats treated with tRORγt-TMD or tGT3-TMD, and the body weight change, the cytotoxicity in blood and hematological biochemistry tests and the autoptic abnormality were not detected. Therefore, tRORγt-TMD treatment did not cause any toxicity with 1 g/kg of injection, and tRORγt-TMD should be a safe reagent with LD50 being more than 1 g/kg.

Each composition comprising the fusion protein according to the present invention may be used with conventional oral formulations such as powders, granules, tablets, capsules, suspensions, syrups, aerosols, etc., externals, suppositories or sterile injection solution. Specifically, diluents or excipients, such as conventional fillers, extenders, binders, wetting agents, disintegrating agents, surfactants, etc. may be used in the preparation of the formulations. Solid formulations for oral administration include, for example, tablets, pellets, powders, granules, capsules, etc., and may be prepared with the addition of at least one or more excipients, for example, starch, calcium carbonate, sucrose, lactose, gelatin, etc. to said protein. In addition, lubricants such as magnesium stearate or talc may be used other than the conventional excipients. Liquid formulation for oral administration includes, for example, suspensions, oral solution, emulsions, syrups, etc., and may be prepared with the addition of several excipients, such as wetting agents, sweetening agents, flavoring agents, preservatives, etc. other than the conventional diluents, such as water and liquid paraffin. Exemplary parenteral formulations include sterile aqueous solution, nonaqueous solvents, suspensions, emulsions, lyophilized formulations and suppositories. Exemplary nonaqueous solvents and suspensions include propylene glycol, polyethylene glycol, vegetable oils such as olive oil and injectable esters such as ethyl oleate. Witepsol, macrogol, tween 61, cocoa buffer, laurinum, glycerogelatin, etc. may be used as suppository bases.

In addition, the dose of the proteins of the present invention may vary according to age, gender and body weight of patients. Generally, the amount of 0.001 to 500 mg/kg, preferably 0.1 to 100 mg/kg may be administered once or several times a day. In addition, the dose of the proteins may be increased or reduced according to the routes of administration, severity of disease, gender, body weight, age, etc. Accordingly, the dose is not intended to limit the scope of the present invention in any aspects.

The present invention has been described with reference to concrete examples. A person skilled in the art would understand that the present invention can be realized as a modified form within a scope not departing from the essential characteristics of the present invention. Accordingly, the disclosed examples must be considered in their illustrative aspect and not their limitative aspect. The scope of the present invention is shown not in the aforesaid explanation but in the appended claims, and all differences within a scope equivalent thereto should be interpreted as being included in the present invention.

INDUSTRIAL APPLICATION

The fusion protein in this invention can treat various diseases associated with malfunctions or defects of the transcription factor.

The invention claimed is:

1. A fusion protein comprising a transcription modulating domain (TMD) of a transcription factor and a protein transduction domain (PTD), wherein the fusion protein is SEQ ID NO:7, to treat a disease selected from the group consisting of multiple sclerosis and rheumatoid arthritis.

2. A fusion protein comprising a TMD of a transcription factor and a PTD, wherein the fusion protein is SEQ ID NO:8, to treat allergic asthma.

3. A nucleic acid encoding the fusion protein according to claim 1 or 2.

4. A vector comprising the nucleic acids according to claim 3.

5. A non-human host cell comprising the vector according to claim 4.

6. The non-human host cell according to claim 5, wherein the host cell is BL21 star (DE3) pLys S.

7. A method for producing the fusion protein of claim 1 or 2, comprising a step of expressing a vector comprising a gene encoding a protein consisting of SEQ ID NO: 7 or 8 in host cells.

8. A pharmaceutical composition for treating a disease selected from the group consisting of multiple sclerosis and rheumatoid arthritis, comprising a fusion protein comprising a TMD of the transcription factor and a PTD, and pharmaceutically acceptable excipients, wherein the fusion protein is SEQ ID NO:7.

9. A pharmaceutical composition for treating allergic asthma, comprising a fusion protein comprising a TMD of a transcription factor and a PTD and pharmaceutically acceptable excipients, wherein the fusion protein is SEQ ID NO: 8.

* * * * *